United States Patent
Amanai

(10) Patent No.: US 10,107,993 B2
(45) Date of Patent: Oct. 23, 2018

(54) WIDE-ANGLE OPTICAL SYSTEM AND IMAGE PICKUP APPARATUS USING THE SAME

(71) Applicant: OLYMPUS CORPORATION, Hachioji-shi, Tokyo (JP)

(72) Inventor: Takahiro Amanai, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 149 days.

(21) Appl. No.: 15/208,123

(22) Filed: Jul. 12, 2016

(65) Prior Publication Data
US 2017/0097498 A1  Apr. 6, 2017

(30) Foreign Application Priority Data
Oct. 1, 2015 (JP) .................. 2015-195959

(51) Int. Cl.
*G02B 13/04* (2006.01)
*G02B 27/00* (2006.01)
*G02B 9/60* (2006.01)

(52) U.S. Cl.
CPC ............. *G02B 13/04* (2013.01); *G02B 9/60* (2013.01); *G02B 27/0025* (2013.01)

(58) Field of Classification Search
CPC ...... G02B 9/60; G02B 13/04; G02B 13/0045; G02B 13/005; G02B 13/06; G02B 27/0025
USPC ........................................ 359/753, 763, 770
See application file for complete search history.

(56) References Cited

U.S. PATENT DOCUMENTS

| | | | |
|---|---|---|---|
| 8,654,457 B2 | 2/2014 | Jin et al. | |
| 2008/0316609 A1* | 12/2008 | Robinson | G02B 13/06 359/664 |
| 2009/0009888 A1* | 1/2009 | Asami | G02B 9/34 359/770 |
| 2014/0104702 A1* | 4/2014 | Yamakawa | G02B 13/18 359/714 |
| 2015/0331224 A1* | 11/2015 | Shih | G02B 9/62 359/756 |

FOREIGN PATENT DOCUMENTS

JP  5282272 B2  9/2013

* cited by examiner

*Primary Examiner* — Jordan Schwartz
(74) *Attorney, Agent, or Firm* — Holtz, Holtz & Volek PC

(57) ABSTRACT

A wide-angle optical system includes in order from an object side to an image side, a first lens having a negative refractive power, a second lens having a negative refractive power, a third lens having a positive refractive power, an aperture stop, a fourth lens having a positive refractive power, and a fifth lens. An object-side surface of the first lens is convex toward the object side, and the following conditional expression (1) is satisfied.

$$1.0 < (R1L + R1R)/(R1L - R1R) \leq 2.0 \qquad (1)$$

where,
R1L denotes a paraxial radius of curvature of the object-side surface of the first lens, and
R1R denotes a paraxial radius of curvature of an image-side surface of the first lens.

13 Claims, 13 Drawing Sheets

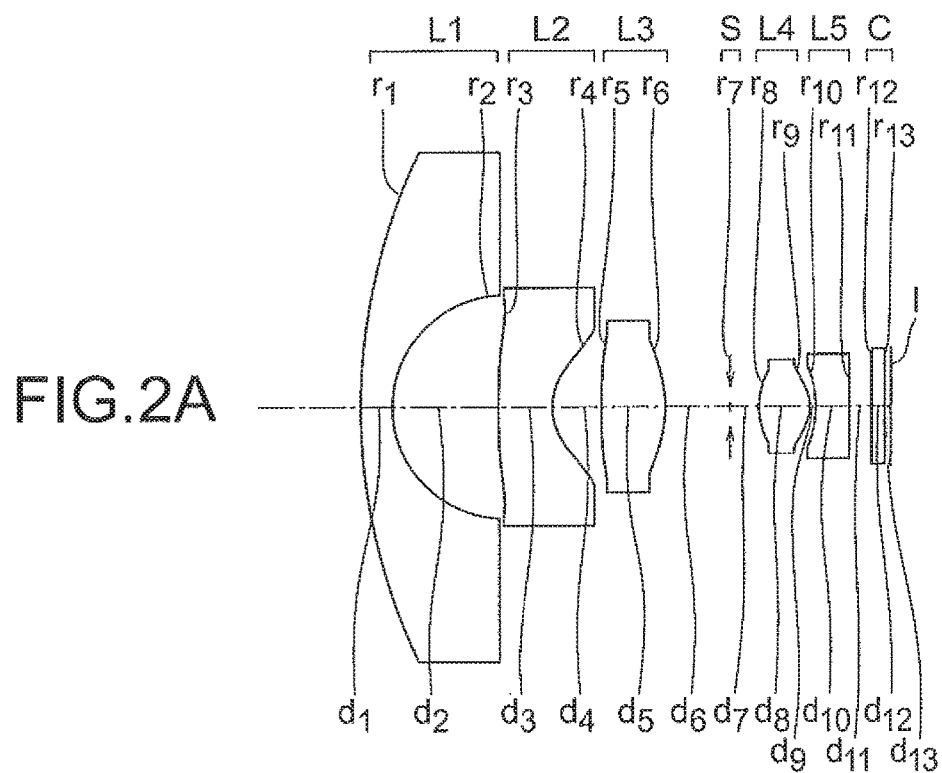
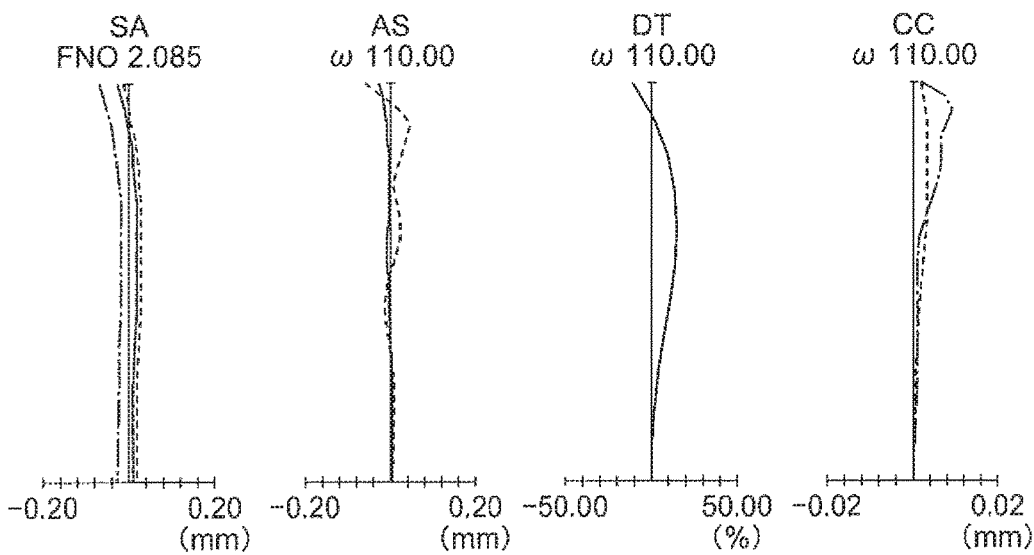

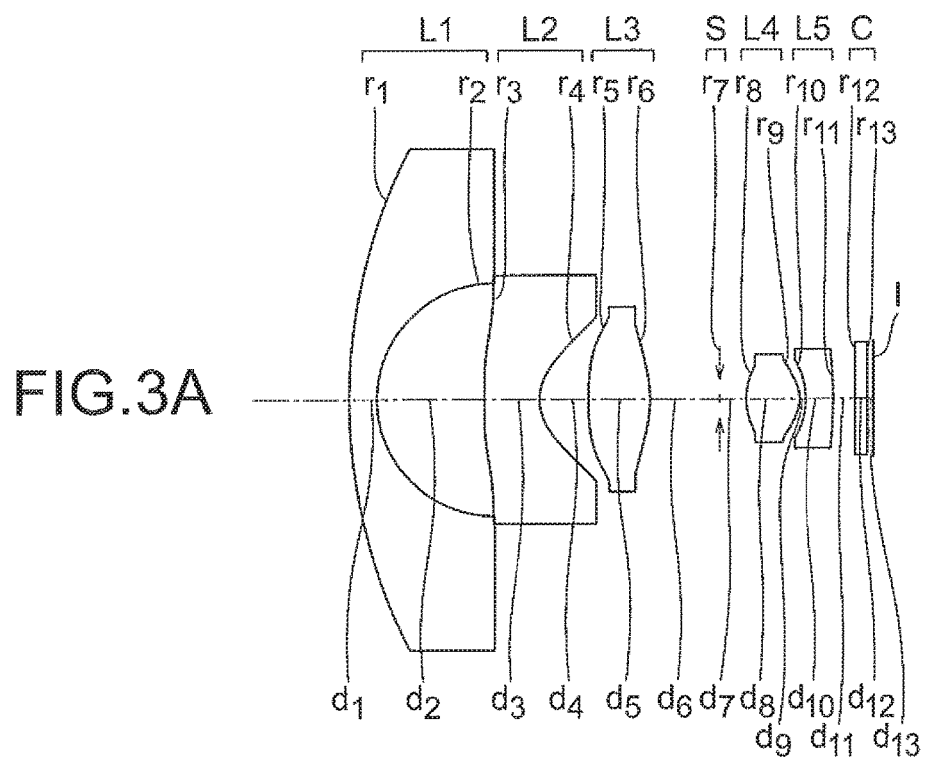
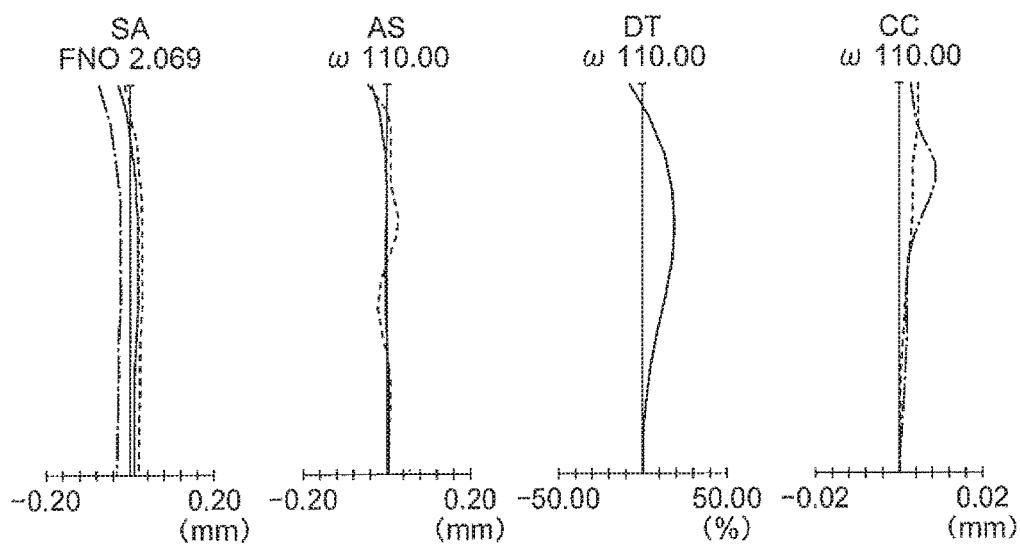

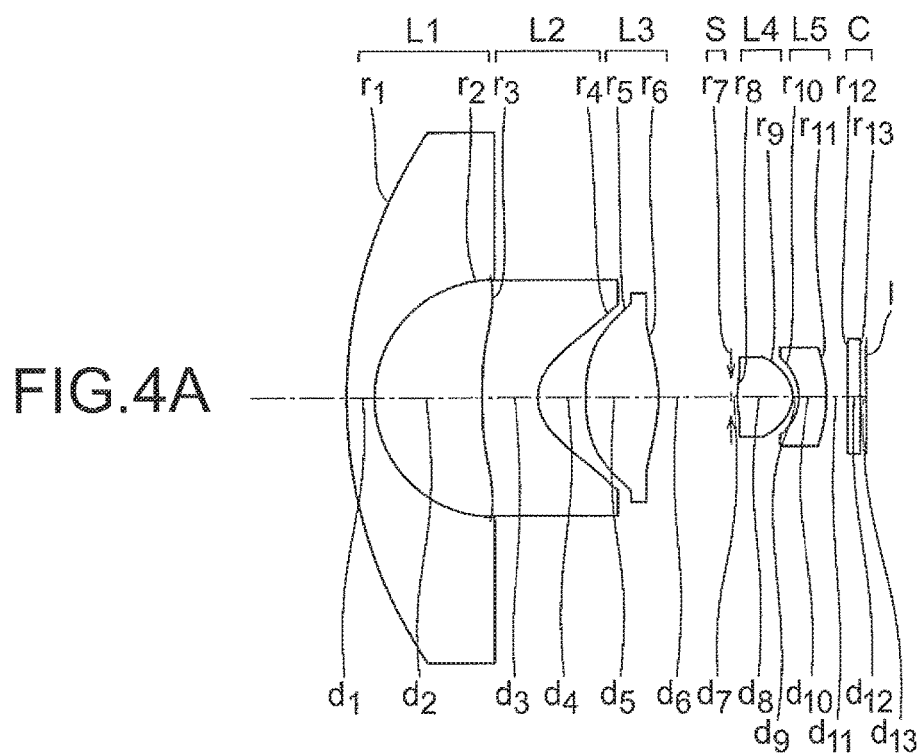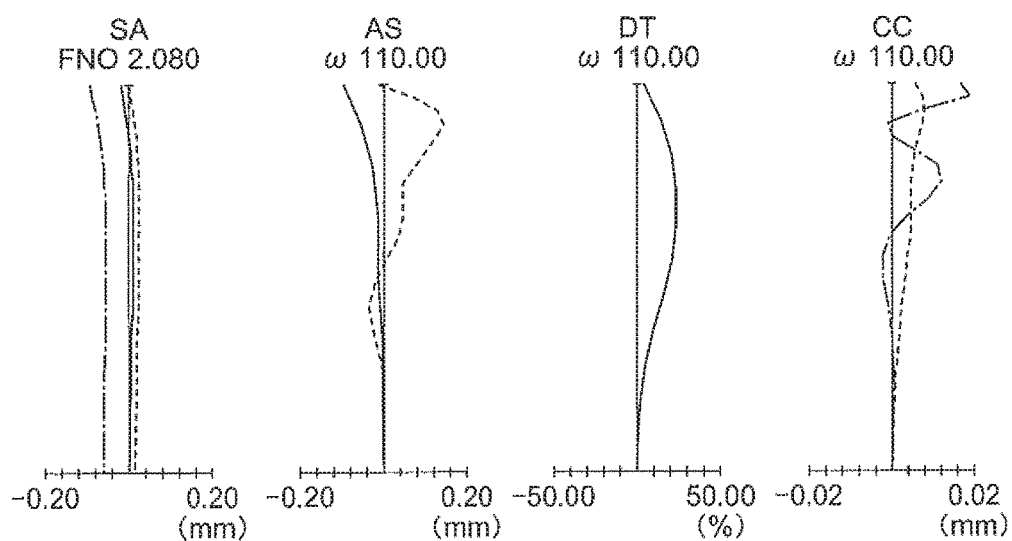

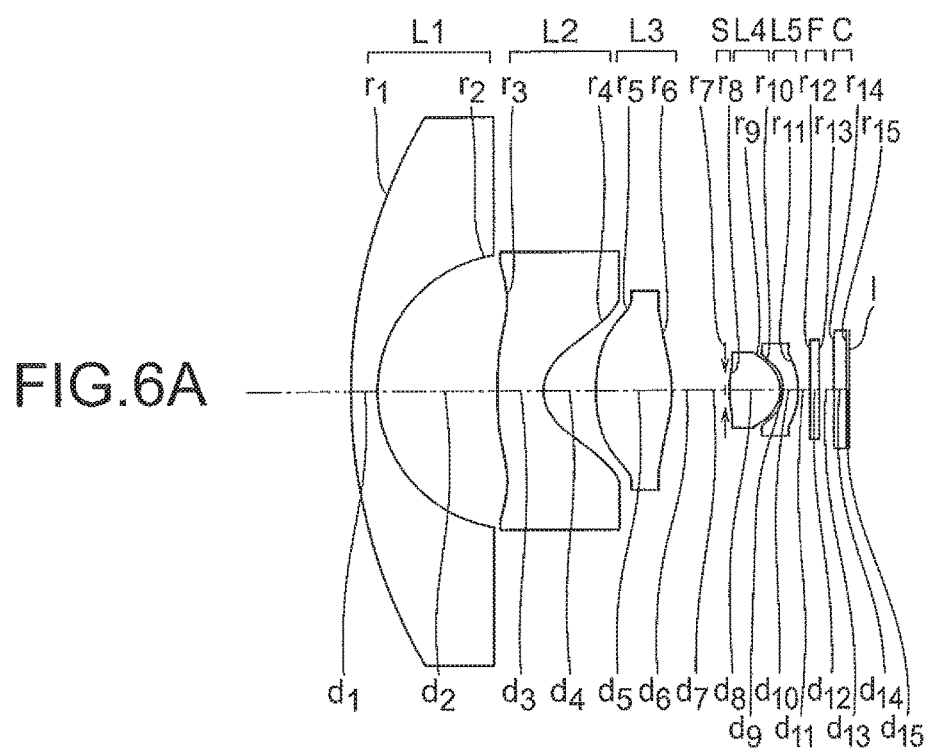
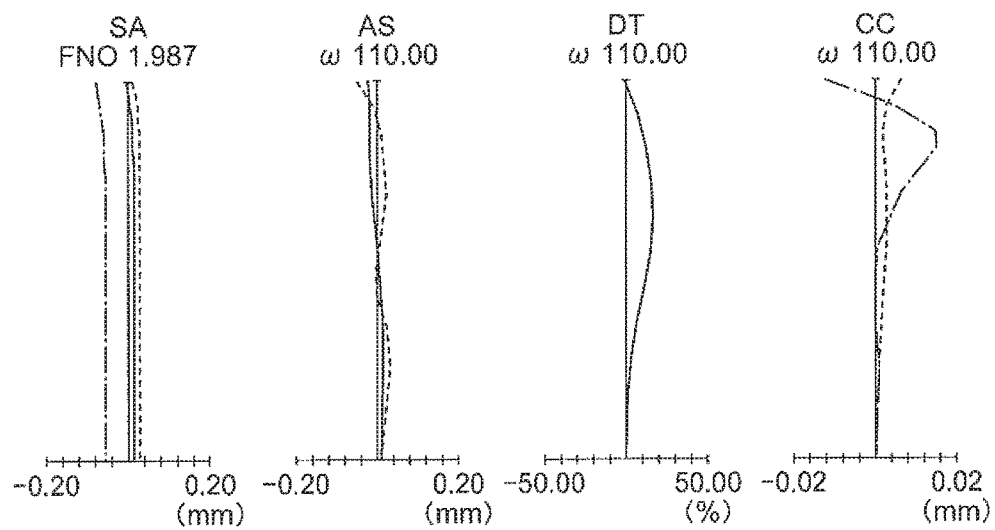

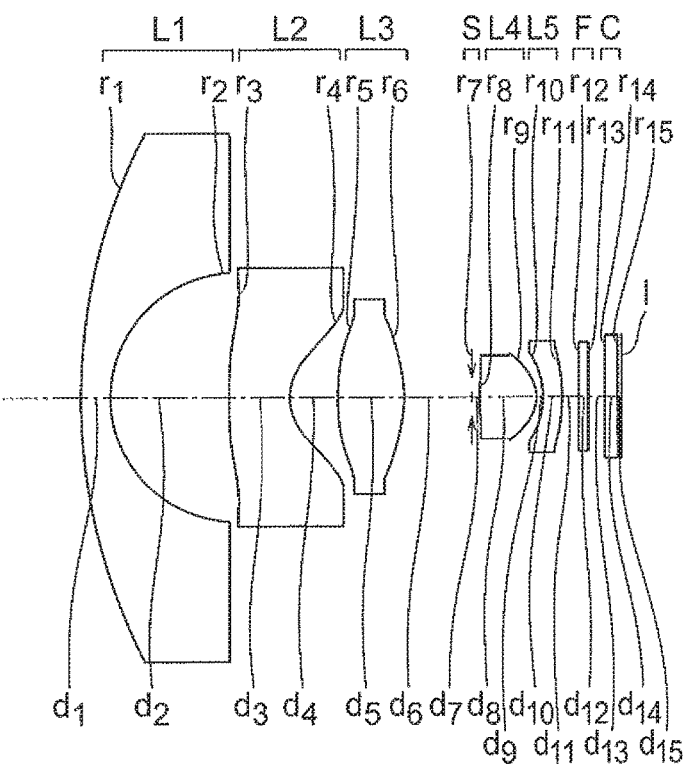
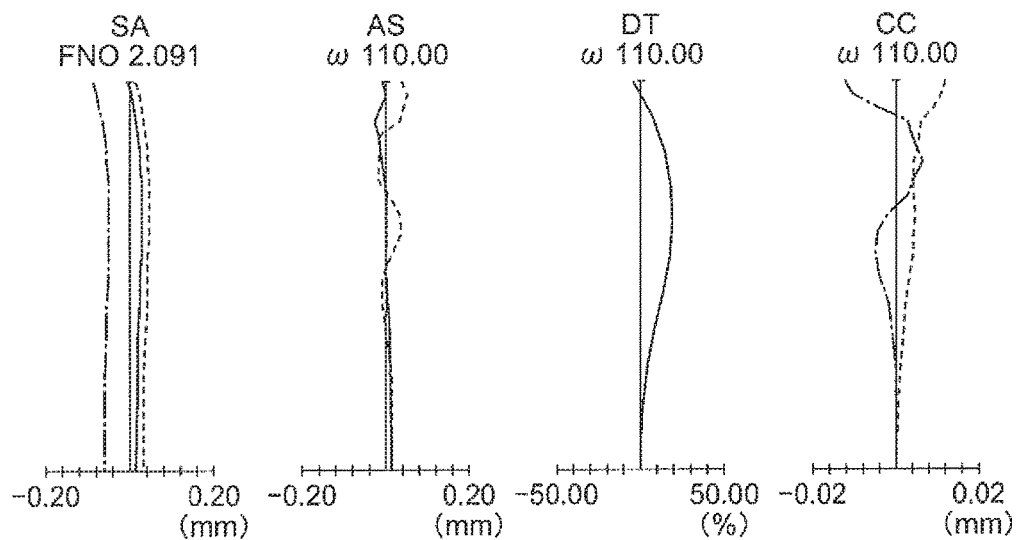

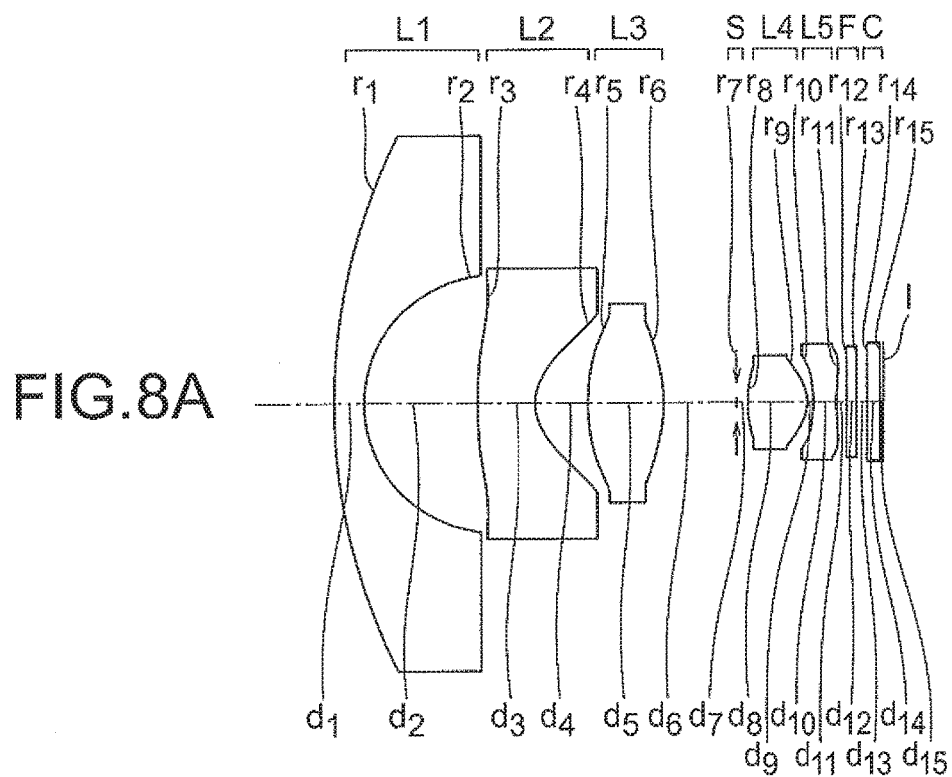
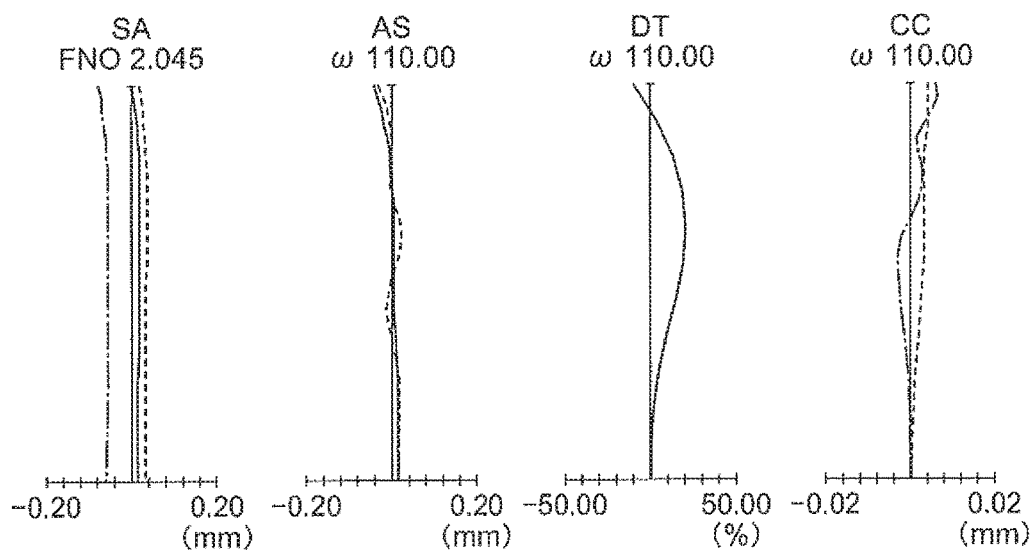

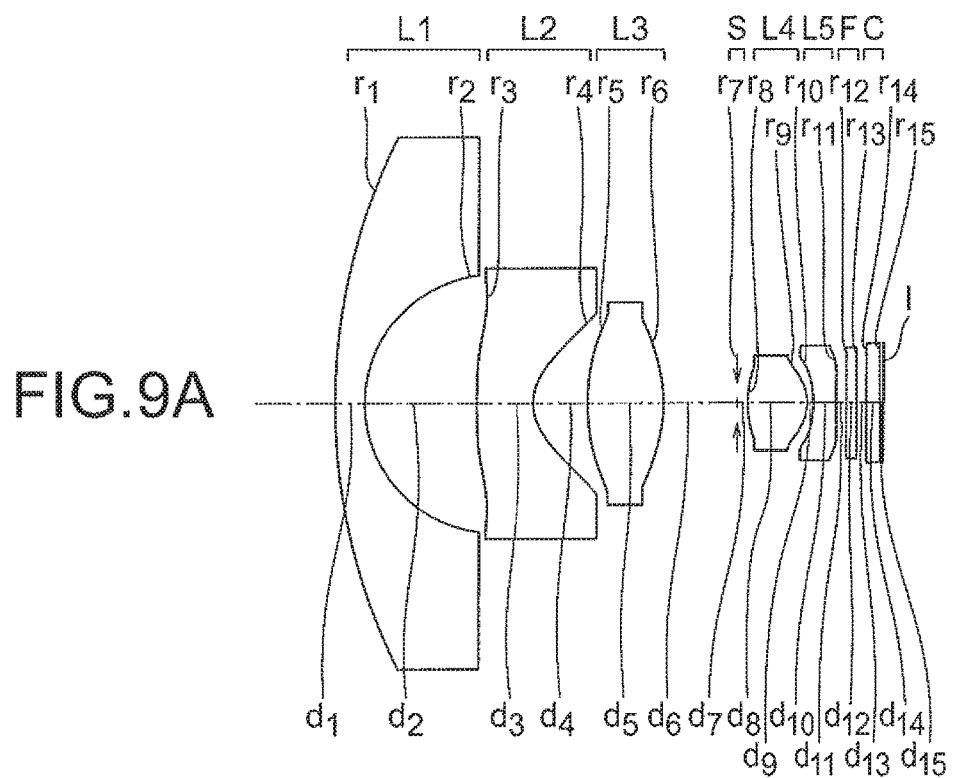
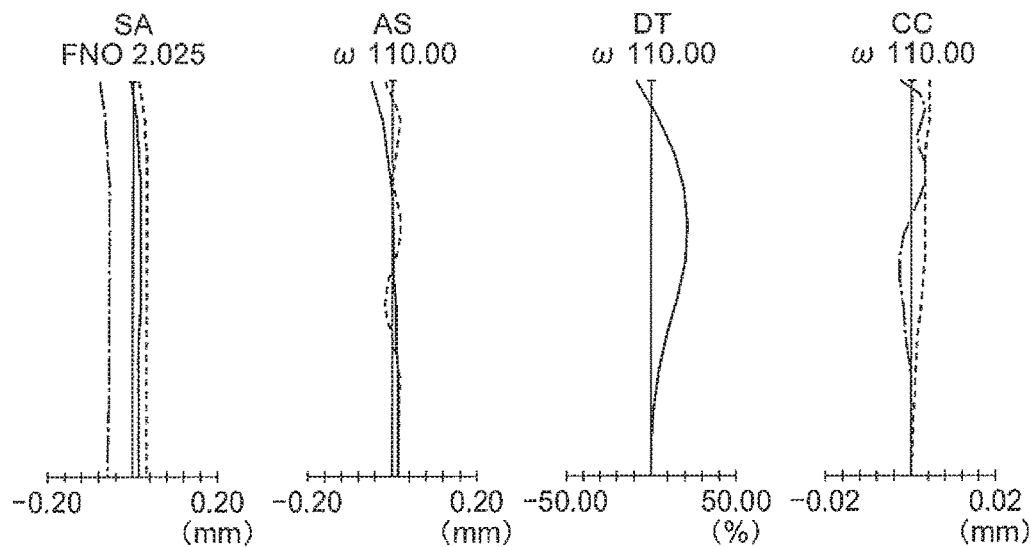

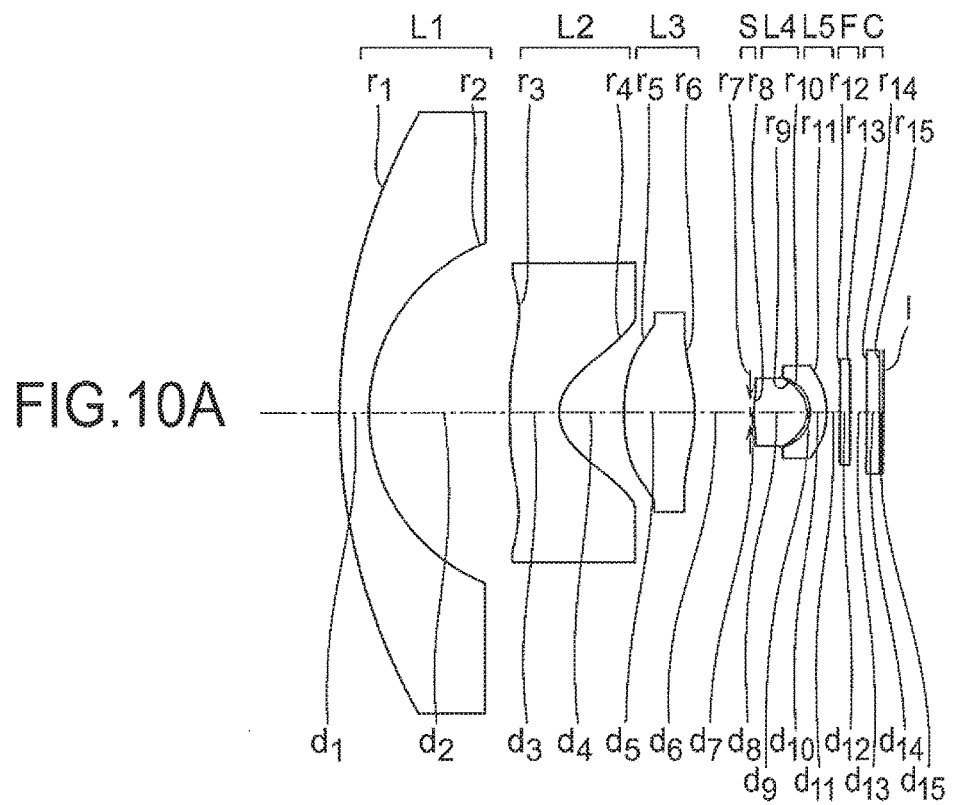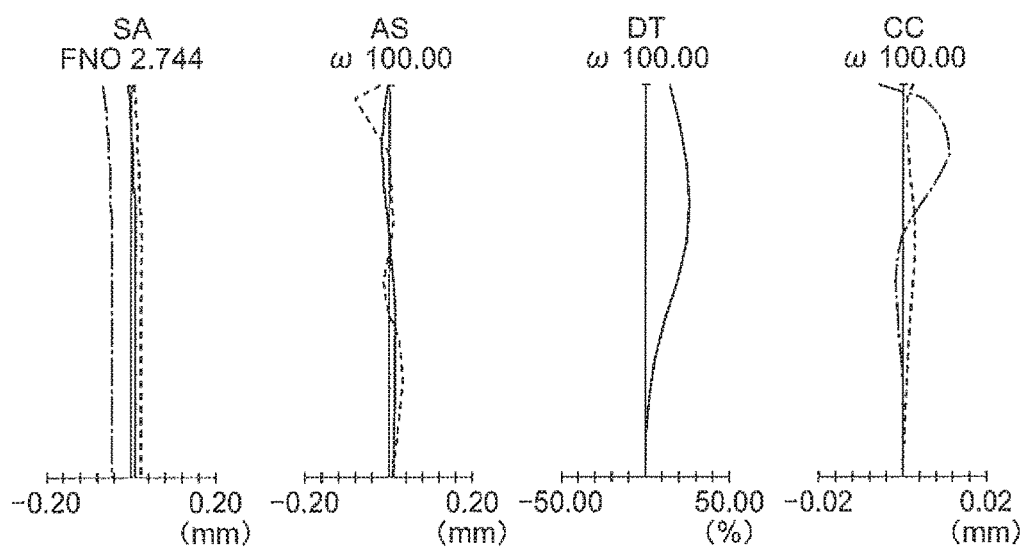

WIDE-ANGLE OPTICAL SYSTEM AND IMAGE PICKUP APPARATUS USING THE SAME

CROSS-REFERENCE TO RELATED APPLICATION

The present application is based upon and claims the benefit of priority from the prior Japanese Patent Application No. 2015-195959 filed on Oct. 1, 2015; the entire contents of which are incorporated herein by reference.

BACKGROUND OF THE INVENTION

Field of the Invention

The present invention relates to a wide-angle optical system and an image pickup apparatus using the same.

Description of the Related Art

A wide-angle optical system having a comparatively wide angle of view has been disclosed in Japanese Patent No. 5282272. This wide-angle optical system includes in order from an object side, a front unit, a stop, and a rear unit. The front unit includes in order from the object side, a first lens having a negative refractive power, a second lens having a negative refractive power, and a third lens having a positive refractive power. The rear unit includes in order from the object side, a fourth lens having a positive refractive power and a fifth lens having a negative refractive power.

SUMMARY OF THE INVENTION

A wide-angle optical system according to an aspect of the present invention comprises in order from an object side to an image side,
a first lens having a negative refractive power,
a second lens having a negative refractive power,
a third lens having a positive refractive power,
an aperture stop,
a fourth lens having a positive refractive power, and
a fifth lens, wherein
an object-side surface of the first lens is convex toward the object side, and
the following conditional expression (1) is satisfied:

$$1.0<(R1L+R1R)/(R1L-R1R)\leq 2.0 \quad (1),$$

where,
R1L denotes a paraxial radius of curvature of the object-side surface of the first lens, and
R1R denotes a paraxial radius of curvature of an image-side surface of the first lens.

Moreover, a wide-angle optical system according another aspect of the present invention comprises in order from an object side to an image side,
a first lens having a negative refractive power,
a second lens having a negative refractive power,
a third lens having a positive refractive power,
an aperture stop,
a fourth lens having a positive refractive power, and
a fifth lens, wherein
an object-side surface of the first lens is convex toward the object side, and
the following conditional expression (2) is satisfied:

$$1.7\leq D34/FL\leq 7.0 \quad (2),$$

where,
D34 denotes a distance on an optical axis from an image-side surface of the third lens up to an object-side surface of the fourth lens, and
FL denotes a focal length of the overall wide-angle optical system.

Moreover, a wide-angle optical system according to still another aspect of the present invention comprises in order from an object side to an image side,
a first lens having a negative refractive power,
a second lens having a negative refractive power,
a third lens having a positive refractive power,
an aperture stop,
a fourth lens having a positive refractive power, and
a fifth lens, wherein
an object-side surface of the first lens is convex toward the object side, and
the following conditional expression (3) is satisfied.

$$-0.4\leq (R3L+R3R)/(R3L-R3R)\leq 2.0 \quad (3)$$

where,
R3L denotes a paraxial radius of curvature of an object-side surface of the third lens, and
R3R denotes a paraxial radius of curvature of an image-side surface of the third lens.

Moreover, a wide-angle optical system according to still another aspect of the present invention comprises in order from an object side to an image side,
a first lens having a negative refractive power,
a second lens having a negative refractive power,
a third lens having a positive refractive power,
an aperture stop,
a fourth lens having a positive refractive power, and
a fifth lens having a negative refractive power, wherein
an object-side surface of the first lens is convex toward the object side, and
the following conditional expression (4) is satisfied:

$$-5.0\leq (R5L+R5R)/(R5L-R5R)\leq -0.37 \quad (4),$$

where,
R5L denotes a paraxial radius of curvature of an object-side surface of the fifth lens, and
R5R denotes a paraxial radius of curvature of an image-side surface of the fifth lens.

Moreover, an image pickup apparatus according to the present invention comprises
the abovementioned wide-angle optical system, and
an image pickup element.

BRIEF DESCRIPTION OF THE DRAWINGS

FIG. 2A is a lens cross-sectional view of a wide-angle optical system according to an example 2, and FIG. 2B, FIG. 2C, FIG. 2D, and FIG. 2E are aberration diagrams of the wide-angle optical system according to the example 2;

FIG. 3A is a lens cross-sectional view of a wide-angle optical system according to an example 3, and FIG. 3B, FIG. 30, FIG. 3D, and FIG. 3E are aberration diagrams of the wide-angle optical system according to the example 3;

FIG. 4A is a lens cross-sectional view of a wide-angle optical system according to an example 4, and FIG. 4B, FIG. 4C, FIG. 4D, and FIG. 4E are aberration diagrams of the wide-angle optical system according to the example 4;

FIG. 5B, FIG. 5C, FIG. 5D, and FIG. 5S are aberration diagrams of the wide-angle optical system according to the example 5;

FIG. 6A is a lens cross-sectional view of a wide-angle optical system according to an example 6, and FIG. 6B, FIG. 6C, FIG. 6D, and FIG. 6S are aberration diagrams of the wide-angle optical system according to the example 6;

FIG. 7A is a lens cross-sectional view of a wide-angle optical system according to an example 7, and FIG. 7B, FIG. 7C, FIG. 7D, and FIG. 7E are aberration diagrams of the wide-angle optical system according to the example 7;

FIG. 8A is a lens cross-sectional view of a wide-angle optical system according to an example 8, and FIG. 8B, FIG. 8C, FIG. 8D, and FIG. 8E are aberration diagrams of the wide-angle optical system according to the example 8;

FIG. 9A is a lens cross-sectional view of a wide-angle optical system according to an example 9, and FIG. 9B, FIG. 9C, FIG. 9D, and FIG. 9S are aberration diagrams of the wide-angle optical system according to the example 9;

FIG. 10A is a lens cross-sectional view of a wide-angle optical system according to an example 10, and FIG. 10B, FIG. 10C, FIG. 10D, and FIG. 10E are aberration diagrams of the wide-angle optical system according to the example 10;

DETAILED DESCRIPTION OF THE INVENTION

Figure 1A:
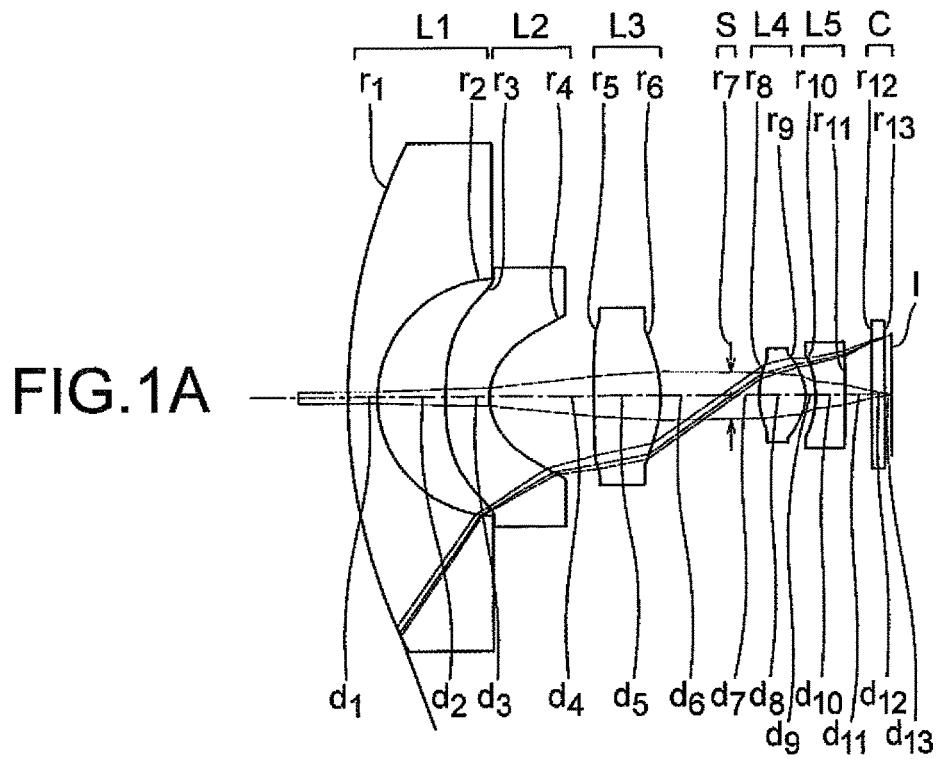
FIG. 1A is a lens cross-sectional view of a wide-angle optical system according to an example 1.
Figures 1B, 1C, 1D, 1E:
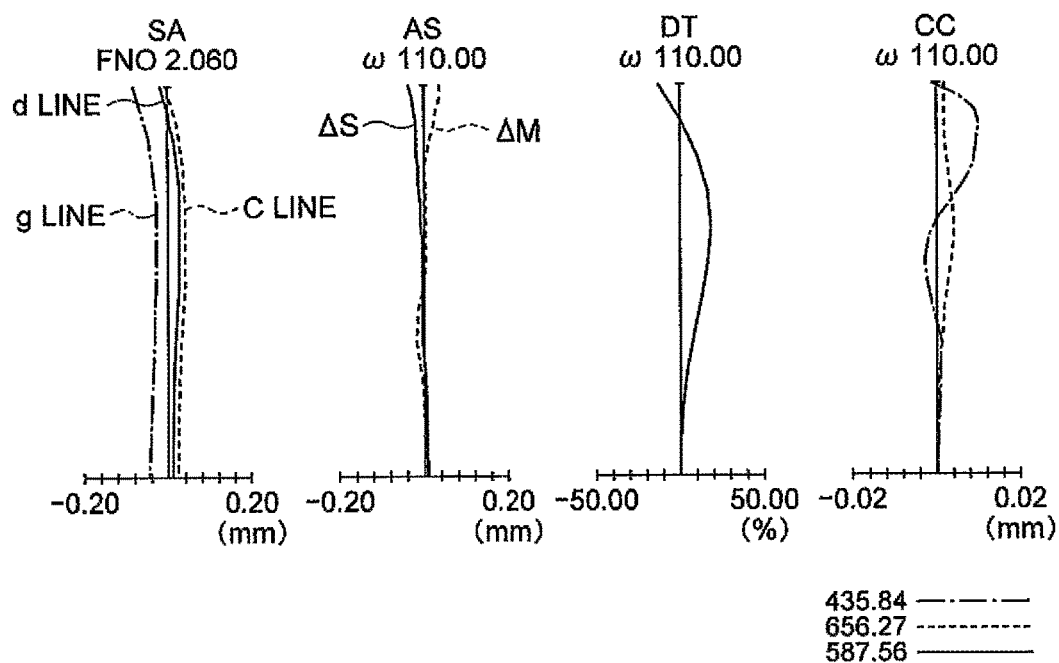
FIG. 1B, FIG. 1C, FIG. 1D, and FIG. 1E are aberration diagrams of the wide-angle optical system according to the example 1.
Figure 5A:
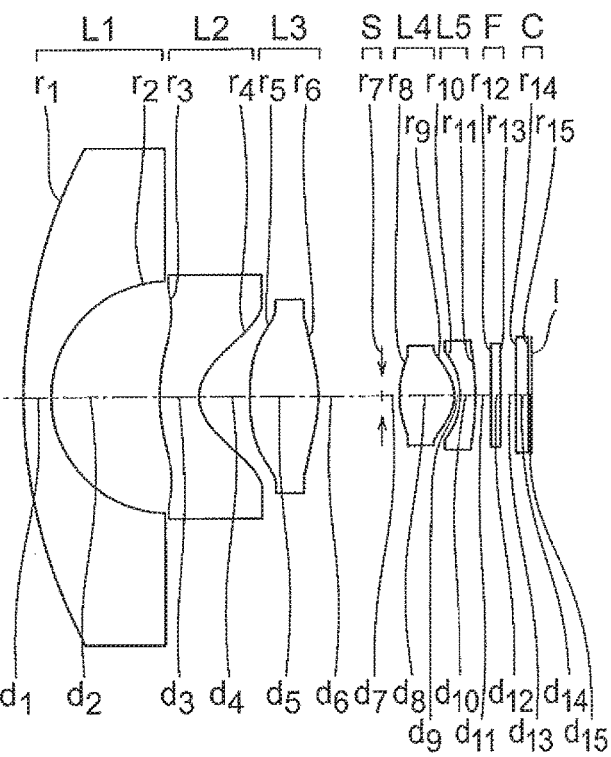
FIG. 5A is a lens cross-sectional view of a wide-angle optical system according to an example 5.
Figures 5B, 5C, 5D, 5E:
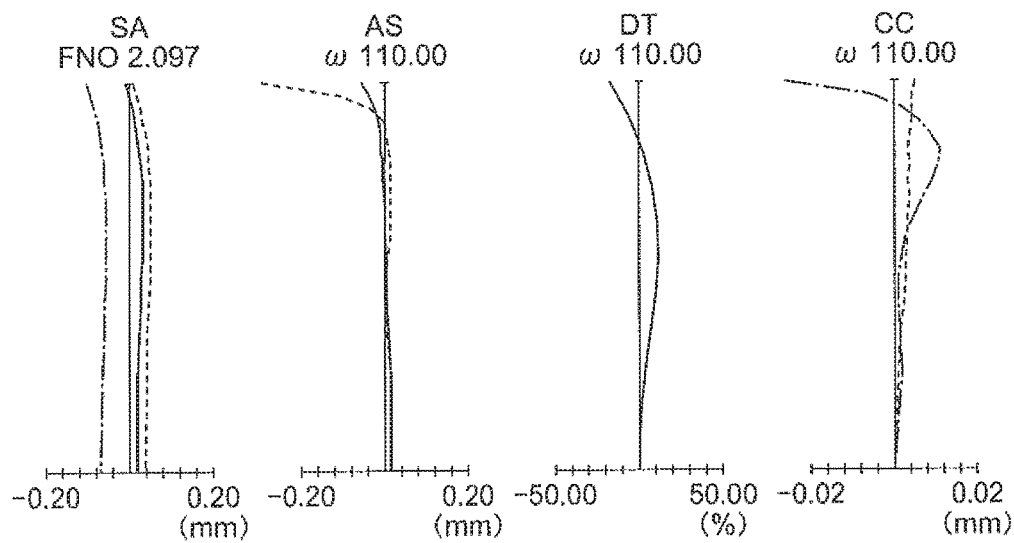

Prior to the explanation of examples, action and effect of embodiments according to certain aspects of the present invention will be described below. In the explanation of the action and effect of the embodiments concretely, the explanation will be made by citing concrete examples. However, similar to a case of the examples to be described later, aspects exemplified thereof are only some of the aspects included in the present invention, and there exists a large number of variations in these aspects. Consequently, the present invention is not restricted to the aspects that will be exemplified.

Wide-angle optical systems according to embodiments from a first embodiment to a fourth embodiment will be described below. The wide-angle optical systems according to these embodiments have a common basic arrangement. Therefore, basic arrangement which is common for the wide-angle optical systems according to the embodiments from the first embodiment to the fourth embodiment will be described below.

In the basic arrangement, an optical system includes in order from an object side to an image side, a first lens having a negative refractive power, a second lens having a negative refractive power, a third lens having a positive refractive power, an aperture stop, a fourth lens having a positive refractive power, and a fifth lens, and an object-side surface of the first lens is convex toward the object side.

In the basic arrangement, the first lens, the second lens, and the third lens are disposed on the object side of the aperture stop, and the fourth lens and the fifth lens are disposed on the image side of the aperture stop. Moreover, a refractive power of a lens unit which includes the first lens, the second lens, and the third lens (hereinafter, referred to as 'the front unit') is a negative refractive power, and a refractive power of a lens unit which includes the fourth lens and the fifth lens (hereinafter, referred to as 'the rear unit') is a positive refractive power.

An optical system in which, the aperture stop is sandwiched between the front unit and the rear unit, and the refractive power of the front unit positioned on the object side of the aperture stop is a negative refractive power, and the refractive power of the rear unit positioned on the image side of the aperture stop is a positive refractive power, is an optical system of a retro-focus type. In such manner, an optical system a retro-focus type has been adopted in the basic arrangement. The optical system of a retro-focus type has a peculiarity that an angle of view is wide. Therefore, even in the basic arrangement, it is possible to realize widening of the angle of view.

Moreover, in the basic arrangement, the object-side surface of the first lens is convex toward the object side. By making such arrangement, when light with a large angle of view is incident on the first lens, it is possible to make an angle of incidence small. As a result, even for the light with a large angle of view, it is possible to suppress an occurrence of an off-axis aberration. Therefore, it is possible to make the angle of view larger without deteriorating aberration.

A wide-angle optical system according to the first embodiment will be described below. The wide-angle optical system according to the first embodiment has the above-mentioned basic arrangement, and also the following conditional expression (1) is satisfied:

$$1.0 < (R1L+R1R)/(R1L-R1R) \leq 2.0 \qquad (1),$$

where,

R1L denotes a paraxial radius of curvature of the object-side surface of the first lens, and R1R denotes a paraxial radius of curvature of an image-side surface of the first lens.

First lens in particular, plays an extremely important role in realizing the widening of the angle of view. As the widening of the angle of view is carried on, an off-axis aberration, particularly an astigmatism, is susceptible to occur. By satisfying conditional expression (1), it is possible to suppress an occurrence of astigmatism when the angle of view was made large. As a result, it is possible to realize a wide-angle optical system with the angle of view of 220° and F-number of 2.0 for example.

By making so as not to exceed an upper limit value of conditional expression (1), it is possible to widen the angle of view without deteriorating the off-axis aberration. Moreover, by making so as not to fall below a lower limit value of conditional expression (1), it is possible to suppress an occurrence of the astigmatism.

The first lens has a negative refractive power, and the object-side surface thereof is convex toward the object side. Consequently, a shape of the first lens becomes a meniscus shape. When exceeding the upper limit value of conditional expression (1), a difference between the paraxial radius of curvature of the object-side surface and the paraxial radius of curvature of the image-side surface becomes small.

In this case, since the negative refractive power of the first lens becomes small, the negative refractive power on the object side of the aperture stop is inadequate. As a result, the angle of view becomes small. To compensate the inadequate negative refractive power, the refractive power of the second lens has to be made large. However, when the negative refractive power of the second lens is made large, a coma and the astigmatism are deteriorated. Therefore, it is not preferable to exceed the upper limit value of conditional expression (1).

When falling below the lower limit value of conditional expression (1), the difference between the paraxial radius of curvature of the object-side surface and the paraxial radius of curvature of the image-side surface becomes large. In this case, the astigmatism occurs substantially. Therefore, it is not preferable to fall below the lower limit value of conditional expression (1).

It is preferable that the following conditional expression (1') is satisfied instead of conditional expression (1).

$$1.2<(R1L+R1R)/(R1L-R1R)\leq 1.95 \qquad (1')$$

It is more preferable that the following conditional expression (1") is satisfied instead of conditional expression (1).

$$1.3<(R1L+R1R)/(R1L-R1R)\leq 1.9 \qquad (1'')$$

A wide-angle optical system according to the second embodiment will be described below. The wide-angle optical system according to the second embodiment has the abovementioned basic arrangement, and also the following conditional expression (2) is satisfied:

$$1.7\leq D34/FL\leq 7.0 \qquad (2),$$

where,

D34 denotes a distance on an optical axis from an image-side surface of the third lens up to an object-side surface of the fourth lens, and FL denotes a focal length of the overall wide-angle optical system.

As mentioned above, in the basic arrangement, the optical system of the retro-focus type has been adopted. In the optical system of the retro-focus type, a distance between a front unit and a rear unit is involved substantially in the refractive power of the overall optical system. Concretely, in the optical system of the retro-focus type, wider the distance between the front unit and the rear unit, stronger is the refractive power the overall optical system. As it is possible to make refractive of the overall optical system large, it is also possible to make the angle of view large.

In the basic arrangement, the third lens is positioned nearest to an image in the front unit, and the fourth lens is disposed nearest to an object in the rear unit. Therefore, in the basic arrangement, the distance on the optical axis from the image-side surface of the third lens up to the object-side surface of the fourth lens (hereinafter, referred to as 'the predetermined distance') plays an extremely important role in realizing the widening of the angle of view.

As mentioned above, for realizing the widening of the angle of view, it is preferable to make the predetermined distance long. However, when the predetermined distance is made long, the third lens goes away from the aperture stop. In this case, since a height of a light ray passing through the third lens becomes high, the off-axis aberration is deteriorated. Therefore, it is necessary to carry out the setting of the predetermined distance upon taking into consideration achieving both of the widening of the angle of view and a favorable aberration correction. By satisfying conditional expression (2), it is possible to achieve both of the widening of the angle of view and the favorable aberration correction.

By making so as not to exceed an upper limit value of conditional expression (2), it is possible to lower the height of the light ray passing through the third lens. As a result, it is possible to suppress an occurrence of the off-axis aberration, particularly the astigmatism and the coma. By making so as not to fall below a lower limit value of conditional expression (2), it is possible to secure adequately the refractive power of the overall optical system. As a result, it is possible to secure a wide angle of view.

When falling below the lower limit value of conditional expression (2), the refractive power of the overall optical system cannot be secured adequately. For achieving adequate refractive power, it is preferable to make the refractive power of the first lens large. However, when the refractive power of the first lens is made large, the coma and the astigmatism are deteriorated. Therefore, it is not preferable to fall below the lower limit value of conditional expression (2)

It is preferable that the following conditional expression (2') is satisfied instead of conditional expression (2).

$$2.0\leq D34/FL\leq 6.0 \qquad (2')$$

Moreover, it is more preferable that the following conditional expression (2") is satisfied instead of conditional expression. (2)

$$2.3\leq D34/FL\leq 5.0 \qquad (2'')$$

A wide-angle optical system according to the third embodiment will be described below. The wide-angle optical system according to the third embodiment has the abovementioned basic arrangement, and also the following conditional expression (3) is satisfied:

$$-0.4\leq (R3L+R3R)/(R3L-R3R)\leq 2.0 \qquad (3),$$

where,

R3L denotes a paraxial radius of curvature of an object-side surface of the third lens, and R3R denotes a paraxial radius of curvature of an image-side surface of the third lens.

For making the F-number small, it is significant to suppress an occurrence of aberration in the third lens. The aberration that is susceptible to occur in the third lens is a spherical aberration, the coma, and the astigmatism. Consequently, it is significant to let a shape of the third lens such that an occurrence of these aberrations is suppressed. By satisfying conditional expression (3), it is possible to suppress the occurrence of these aberrations.

By making so as not exceed an upper limit value of conditional expression (3), it is possible to suppress the occurrence of the astigmatism. By making so as not to fall below a lower limit value of conditional expression (3), it is possible to suppress the occurrence of the spherical aberration and the coma.

For suppressing the occurrence of astigmatism, it is preferable that a lens surface is concentric (hereinafter, referred to as 'the concentric state') with respect to the aperture stop. When exceeding the upper limit value of conditional expression (3), since the paraxial radius of curvature of the image-side surface becomes smaller as compared to the paraxial radius of curvature of the object-side surface, deviation from the concentric state becomes large at the image-side surface. As a result, the astigmatism is susceptible to occur.

For suppressing the occurrence of the spherical aberration and the coma, it is preferable to make an arrangement such that a curvature center of each optical surface is disposed in a direction in which a light beam is converged. In other words, for making a shape that is adapted to the abovementioned arrangement, it is preferable that the paraxial radius of curvature of the image-side surface is smaller than the paraxial radius of curvature of the object-side surface. When falling below the lower limit value of conditional expression (3), the paraxial radius of curvature of the image-side surface becomes larger as compared to the paraxial radius of curvature of the object-side surface. Consequently, the spherical aberration and the coma become susceptible to occur.

It is preferable that the following conditional expression (3') is satisfied instead of conditional expression (3).

$$-0.2 \leq (R3L+R3R)/(R3L-R3R) \leq 1.5 \quad (3')$$

It is more preferable that the following conditional expression (3") is satisfied instead of conditional expression (3)

$$-0 \leq (R3L+R3R)/(R3L-R3R) \leq 1.2 \quad (3'')$$

A wide-angle optical system according to the fourth embodiment will be described below. The wide-angle optical system according to the fourth embodiment has the abovementioned basic arrangement, and also the following conditional expression (4) is satisfied:

$$-5.0 \leq (R5L+R5R)/(R5L-R5R) \leq -0.37 \quad (4),$$

where,

R5L denotes a paraxial radius of curvature of an object-side surface of the fifth lens, and R5R denotes a paraxial radius of curvature of an image-side surface of the fifth lens.

For making the F-number small, it is significant to suppress an occurrence of spherical aberration and coma and an occurrence of astigmatism. The fifth lens has a function of correcting the spherical aberration, the coma, and the astigmatism. By satisfying conditional expression (4), it is possible to correct the spherical aberration, the coma, and the astigmatism favorably.

By making so as not to exceed an upper limit value of conditional expression (4), it is possible to correct the astigmatism favorably. By making so as not to fall below a lower limit value of conditional expression (4), it is possible to correct the spherical aberration and the coma favorably.

When exceeding the upper limit value of conditional expression (4), the paraxial radius of curvature of the image-side surface becomes smaller as compared to the paraxial radius of curvature of the object-side surface. In this case, deviation from the concentric state becomes large at the image-side surface. As a result, the astigmatism is susceptible to occur.

When falling below the lower limit value of conditional expression (4), the paraxial radius of curvature of the image-side surface becomes larger as compared to the paraxial radius of curvature of the object-side surface, and a curvature centers of surfaces on both sides are disposed on the object side. Consequently, the curvature center of each optical surface is not disposed in a direction in which a light beam is converged, and as a result, the spherical aberration and the coma are susceptible to occur.

It is preferable that the following conditional expression (4') is satisfied instead of conditional expression (4).

$$-4.0 \leq (R5L+R5R)/(R5L-R5R) \leq -0.40 \quad (4')$$

It is more preferable that the following conditional expression (4") is satisfied instead of conditional expression (4), $$-3.0 \leq (R5L+R5R)/(R5L-R5R) \leq -0.43 \quad (4'')$$

In the wide-angle optical systems according to embodiments from the first embodiment to the fourth embodiment (hereinafter, referred to as 'the wide-angle optical system according to the present embodiment'), it is preferable that the following conditional expressions (5) and (6) are satisfied, $$nd2 < nd1 \quad (5), \text{ and}$$

$$0.2 \leq FL1/FL2 \leq 3.8 \quad (6),$$

where, nd1 denotes a refractive index for a d-line of the first lens, nd2 denotes a refractive index for a d-line of the second lens, FL1 denotes a focal length of the first lens, and FL2 denotes a focal length of the second lens.

By satisfying conditional expressions (5) and (6), it is possible to achieve both of widening of the angle of view and correction of various aberrations.

By satisfying conditional expression (5), it is possible to secure a large refractive power without making a paraxial radius of curvature of a lens surface small. Consequently, it is possible to make incident a light ray with a large angle of view. As a result, it is possible to realize the widening of the angle of view.

By making so as not to exceed an upper limit value of conditional expression (6), it is possible to suppress an occurrence of various aberrations, particularly an occurrence of astigmatism and an occurrence of coma, in the second lens. By making so as not to fall below a lower limit value of conditional expression (6), it is possible to suppress an occurrence of various aberrations, particularly an occurrence of astigmatism and an occurrence of distortion, in the first lens.

The refractive index of the second lens is lower than the refractive index of the first lens. In this case, when the upper limit value of conditional expression (6) is exceeded, the refractive power of the second lens becomes large as compared to a case in which, the refractive index of the second lens is higher than the refractive index of the first lens. As a result, an amount astigmatism that occurs and an amount of coma aberration that occurs become large. Therefore, it is not preferable to exceed the upper limit value of conditional expression (6).

The refractive index of the first lens being higher than the refractive index of the second lens, it is easy to achieve a refractive power larger as compared to the refractive power of the second lens. When falling below the lower limit value of conditional expression (6), the refractive power of the first lens becomes excessively large. As a result, the astigmatism and the distortion occur substantially. Therefore, it is not preferable to fall below the lower limit value of conditional expression (6).

It is more preferable that the following conditional expression (6') is satisfied instead of conditional expression (6).

$$0.5 \leq FL1/FL2 \leq 3.7 \quad (6')$$

It is even more preferable that the following conditional expression (6") is satisfied instead of conditional expression (6)

$$1.0 \leq FL1/FL2 \leq 3.6 \quad (6'')$$

In the wide-angle optical system according to the present embodiment, it is preferable that the following conditional expression (7) is satisfied:

$$-2.1 \leq (R2R+R3L)/(R2R-R3L) \leq -0.2 \quad (7),$$

where,

R2R denotes a paraxial radius of curvature of an image-side surface of the second lens, and R3L denotes a paraxial radius of curvature of an object-side surface of the third lens.

When the angle of view of the optical system is widened, the astigmatism and the coma aberration are susceptible to occur. Refraction of a light ray at the second lens and refraction of a light ray at the third lens are associated largely with the occurrence of the astigmatism and the coma. Therefore, for correcting these aberrations favorably, it becomes necessary to maintain an angle of refraction of a light ray at the two lenses to be optimum.

An air lens is formed between the second lens and the third lens. Therefore, for correcting an aberration favorably, optimizing a shape of the air lens becomes significant.

The coma and the astigmatism are susceptible to occur in the object-side surface of the second lens and the image-side surface of the third lens. By making so as not to exceed an upper limit value of conditional expression (7), it is possible to correct favorably the coma and the astigmatism occurring in these surfaces, by the air lens.

The coma and the astigmatism are susceptible to occur even at both surfaces of the air lens, or at the image-side surface of the second lens and the object-side surface of the third lens. By making so as not to fall below a lower limit value of conditional expression (7), an occurrence of coma and an occurrence of astigmatism at two surfaces of the air lens are suppressed.

It is more preferable that the following conditional expression (7') is satisfied instead of conditional expression (7).

$$-2.0 \leq (R2R+R3L)/(R2R-R3L) \leq -0.5 \quad (7')$$

It is even more preferable that the following conditional expression (7") is satisfied instead of conditional expression (7).

$$-1.8 \leq (R2R+R3L)/(R2R-R3L) \leq -0.9 \quad (7")$$

In the wide-angle optical system according to the present embodiment, it is preferable that the following conditional expression (8) is satisfied:

$$4.2 \leq FL3/FL \leq 12.0 \quad (8),$$

where,
FL3 denotes a focal length of the third lens, and
FL denotes a focal length of the overall wide-angle optical system.

For widening the angle of view, it is preferable that the refractive index of the first lens is high, and the refractive power of the first lens is large. However, when such an arrangement is made, it is necessary to correct Petzval's sum by the third lens having a positive refractive power and the fourth lens having a positive refractive power.

In a case of making the F-number small, since correction of mainly a chromatic aberration is carried out in the fourth lens, it is difficult to use the fourth lens for correction of Petzval's sum. Therefore, correction of Petzval's sum is to be carried out mainly in the third lens. By satisfying conditional expression (8), it is possible to correct Petzval's sum favorably.

By making so as not to exceed an upper limit value of conditional expression (8), it is possible to not let Petzval's sum to be corrected inadequately. By making so as not to fall below a lower limit value of conditional expression (8), it is possible to not let Petzval's sum to be corrected excessively.

It is more preferable that the following conditional expression (8') is satisfied instead of conditional expression (8).

$$5.0 \leq FL3/FL \leq 10.0 \quad (8')$$

It is even more preferable that the following conditional expression (8") is satisfied instead of conditional expression (8).

$$5.5 \leq FL3/FL \leq 9.0 \quad (8")$$

In the wide-angle optical system according to the present embodiment, it is preferable that the following conditional expressions (9) and (10) are satisfied:

$$1.7 \leq nd1 \leq 2.1 \quad (9), \text{ and}$$

$$25 \leq vd1 \leq 55 \quad (10),$$

where,
nd1 denotes a refractive index for a d-line of the first lens, and
vd1 denotes Abbe's number for the first lens.

For widening the angle of view, it is significant to make the refractive index of the first lens high. However, when the angle of view is widened, various aberrations, particularly a chromatic aberration of magnification, are susceptible to occur. By satisfying conditional expressions (9) and (10), it is possible to widen the angle of view and to correct the chromatic aberration of magnification.

When falling below a lower limit value of conditional expression (9) and falling below a lower limit value of conditional expression (10), the correction of the chromatic aberration of magnification is inadequate. When exceeding an upper limit value of conditional expression (9) and exceeding an upper limit value of conditional expression (10), since an appropriate glass material is not available, correction of the chromatic aberration of magnification becomes difficult.

In the wide-angle optical system according to the present embodiment, it is preferable that the following conditional expressions (11) and (12) are satisfied:

$$1.45 \leq nd4 \leq 1.65 \quad (11), \text{ and}$$

$$25 \leq vd4 \leq 60 \quad (12),$$

where,
nd4 denotes a refractive index for a d-line of the fourth lens, and
vd4 denotes Abbe's number for the fourth lens.

Since the fourth lens is positioned near the aperture stop, a longitudinal chromatic aberration is susceptible to occur. By satisfying conditional expressions (11) and (12), in a case in which, the F-number is made small, it is possible to correct Petzval's sum favorably and to suppress the longitudinal chromatic aberration.

When falling below a lower limit value of conditional expression (11) and falling below a lower limit value of conditional expression (12), the correction of Petzval's sum and the correction of the longitudinal chromatic aberration are inadequate. When exceeding an upper limit value of conditional expression (11) and exceeding an upper limit value of conditional expression (12), the correction of the Petzval sum and the correction of the longitudinal chromatic aberration become excessive.

In the wide-angle optical system according to the present embodiment, it is preferable that the fifth lens has a negative refractive power.

By the fifth lens having a negative refractive power, an arrangement of refractive power becomes a negative refractive power and a positive refractive power in the front unit, and a positive refractive power and a negative refractive power in the rear unit. In other words, the arrangement of refractive power is symmetric about the aperture stop in between. Consequently, it is possible to suppress an occurrence of various aberrations.

Moreover, by the fifth lens having the negative refractive power, a lens having a negative refractive power is disposed near an image plane. Consequently, it is possible to correct the chromatic aberration favorably.

In the wide-angle optical system according to the present embodiment, it is preferable that the following conditional expression (13) is satisfied:

$$-30 \leq FL5/FL \leq -6 \qquad (13),$$

where,

FL5 denotes a focal length of the fifth lens, and

FL denotes a focal length of the overall wide-angle optical system.

The focal length of the fifth lens is associated with the angle of view, the F-number, and a size of the optical system. Therefore, for small-sizing the optical system while satisfying conditions of a wide angle of view and a small F-number, it is significant to maintain the focal length of the fifth lens to be optimum.

By satisfying conditional expression (13), it is possible to make the optical system small-sized while securing a wide angle of view and a small F-number.

When exceeding an upper limit value of conditional expression (13), since the negative refractive power of the fifth lens becomes excessively large, Petzval's sum is deteriorated. When falling below a lower limit value of conditional expression (13), the negative refractive power of the fifth lens becomes excessively small. In this case, since the symmetry of refractive power is degraded, various aberrations, particularly the longitudinal chromatic aberrations, cannot be corrected sufficiently.

It is more preferable that the following conditional expression (13') is satisfied instead of conditional expression (13)

$$-20 \leq FL5/FL \leq -5 \qquad (13')$$

It is even more preferable that the following conditional expression (13") is satisfied instead of conditional expression (13).

$$-12 \leq FL5/FL \leq -4 \qquad (13")$$

In the wide-angle optical system according to the present embodiment, it is preferable that the following conditional expression (14) is satisfied:

$$15 \leq \Phi 1/FL \leq 30 \qquad (14),$$

where, $\Phi 1$ denotes the maximum effective aperture in the lens, and

FL denotes a focal length of the overall wide-angle optical system.

By satisfying conditional expression (14), it is possible to achieve both of widening of the angle of view and small-sizing of the optical system.

When exceeding an upper limit value of conditional expression (14), since a diameter of the first lens becomes large, small-sizing of the optical system becomes difficult. When falling below a lower limit value of conditional expression (14), the diameter of the first lens becomes small. In this case, since a position of an entrance-pupil is made to be positioned on the object side, widening of the angle of view becomes difficult. Furthermore, the astigmatism and the coma are susceptible to occur.

In the wide-angle optical system according to the present embodiment, it is preferable that the following conditional expressions (15) and (16) are satisfied:

$$200° \leq 2\omega \leq 240° \qquad (15), \text{ and}$$

$$2.5 \leq Fno \leq 1.5 \qquad (16),$$

where, $\omega$ denotes the maximum half angle of view, and

Fno denotes an F-number.

By satisfying conditional expressions (15) and (16), it is possible to make the optical system small, while widening the angle of view and securing a small F-number.

In the wide-angle optical system according to the present embodiment, it is preferable that each of the first lens, the second lens, the third lens, the fourth lens, and the fifth lens is a single lens.

By making such arrangement, it is possible make the optical system small.

In the wide-angle optical system according to the present embodiment, it is preferable that the total number of lens elements is five. Here, lens element refers to a lens which includes a medium of a single refractive index. For instance, doublet cemented lens is a cemented lens which includes two lens elements.

By making such arrangement, it is possible to make the optical system small.

An image pickup apparatus according to the present embodiment comprises the abovementioned wide-angle optical system, and an image pickup element.

According to the image pickup apparatus of the present embodiment, it is possible to acquire a wide-angle image having a high resolution even in a dark location.

The aforementioned wide-angle optical system and the image pickup apparatus may satisfy a plurality of arrangements simultaneously. Making such arrangement is preferable for achieving a favorable wide-angle optical system and the image pickup apparatus. Moreover, combinations of preferable arrangements are voluntary. Furthermore, regarding each conditional expression, only an upper limit value or a lower limit value of a numerical range of a further restricted conditional expression may be restricted.

Examples of the wide-angle optical system will be described below in detail by referring to the accompanying diagrams. However, the present invention should not be construed as being limited to the following examples.

The diagrams will be described below. In diagrams of examples from a first example to a tenth example, FIG. 1A, FIG. 2A, FIG. 3A, FIG. 4A, FIG. 5A, FIG. 6A, FIG. 7A, FIG. 8A, FIG. 9A, and FIG. 10A are cross-sectional views of wide-angle optical systems. In the diagrams, C denotes a cover glass, and F denotes a filter.

Aberration diagrams will be described below. FIG. 1B, FIG. 2B, FIG. 3S, FIG. 4B, FIG. 5B, FIG. 6B, FIG. 7B, FIG. 8B, FIG. 9B, and FIG. 10B show a spherical aberration (SA), FIG. 1C, FIG. 2C, FIG. 3C, FIG. 4C, FIG. 5C, FIG. 6C, FIG. 7C, FIG. 8C, FIG. 9C, and FIG. 10C show an astigmatism (AS), FIG. 1D, FIG. 2D, FIG. 3D, FIG. 4D, FIG. 5D, FIG. 6D, FIG. 7D, FIG. 8D, FIG. 9D, and FIG. 10D show a distortion (DT), and FIG. 1E, FIG. 2E, FIG. 3E, FIG. 4E, FIG. 5E, FIG. 6E, FIG. 7E, FIG. 8E, FIG. 9E, and FIG. 10E show a chromatic aberration of magnification (CC).

The lens cross-sectional views, the aberration diagrams, and the following numerical value examples are at the time of focusing to an object at infinity.

The distortion is calculated by using a stereographic projection method. In the stereographic projection method, an ideal image height is expressed by the following expression (A)

$$Y=2\times f\times \tan(\omega/2) \quad (A)$$

where,
Y denotes the ideal image height,
f denotes a focal length, and
ω denotes a half angle of view.

Consequently, it is possible to calculate the distortion from the following expression (B) by using the ideal image height Y and an actual image height y.

$$DT\ (\%)=(y-Y)/Y\times 100 \quad (B)$$

In examples in which, the filter F has not been disposed, a multi-layer film for restricting wavelength region may be applied to a surface of the cover glass. Moreover, a low-pass filter effect may be imparted to the cover glass.

A wide-angle optical system according to the example 1 includes in order from an object side, a negative meniscus lens L1 having a convex surface directed toward the object side, a negative meniscus lens L2 having a convex surface directed toward the object side, a biconvex positive lens L3, a biconvex positive lens L4, and a negative meniscus lens L5 having a convex surface directed toward an image side.

An aperture stop S is disposed between the biconvex positive lens L3 and the biconvex positive lens L4.

An aspheric surface is provided to a total of six surfaces namely, both side surfaces of the negative meniscus lens L2, both side surfaces of the biconvex positive lens L3, and both side surfaces of the biconvex positive lens L4.

A wide-angle optical system according to the example 2 includes in order from an object side, a negative meniscus lens L1 having a convex surface directed to the object side, a biconcave negative lens L2, a biconvex positive lens L3, a biconvex positive lens L4, and a negative meniscus lens L5 having a convex surface directed toward an image side.

An aperture stop S is disposed between the biconvex positive lens L3 and the biconvex positive lens L4.

An aspheric surface is provided to a total of six surfaces namely, both side surfaces of the biconcave negative lens L2, both side surfaces of the biconvex positive lens L3, and both side surfaces of the biconvex positive lens L4.

A wide-angle optical system according to the example 3 includes in order from an object side, a negative meniscus lens L1 having a convex surface directed toward the object side, a negative meniscus lens L2 having a convex surface directed toward the object side, a biconvex positive lens L3, a biconvex positive lens L4, and a negative meniscus lens L5 having a convex surface directed toward an image side.

An aperture stop S is disposed between the biconvex positive lens L3 and the biconvex positive lens L4

An aspheric surface is provided to a total of six surfaces namely, both side surfaces of the negative meniscus lens L2, both side surfaces of the biconvex positive lens L3, and both side surfaces of the biconvex positive lens L4.

A wide-angle optical system according to the example 4 includes in order from an object side, a negative meniscus lens L1 having a convex surface directed toward the object side, negative meniscus lens L2 having a convex surface directed toward the object side, a biconvex positive lens L3, a biconvex positive lens L4, and a negative meniscus lens L5 having a convex surface directed toward an image side.

An aperture stop S is disposed between the biconvex positive lens L3 and the biconvex positive lens L4.

An aspheric surface is provided to a total of six surfaces namely, both side surfaces of the negative meniscus lens L2, both side surfaces of the biconvex positive lens L3, and both side surfaces of the biconvex positive lens L4.

A wide-angle optical system according to the example 5 includes in order from an object side, a negative meniscus lens L1 having a convex surface directed toward the object side, a negative meniscus lens L2 having a convex surface directed toward the object side, a biconvex positive lens L3, a biconvex positive lens L4, and a negative meniscus lens L5 having a convex surface directed toward an image side.

An aperture stop S is disposed between the biconvex positive lens L3 and the biconvex positive lens L4.

An aspheric surface is provided to a total of six surfaces namely, both side surfaces of the negative meniscus lens L2, both side surfaces of the biconvex positive lens L3, and both side surfaces of the biconvex positive lens L4.

A wide-angle optical system according to the example 6 includes in order from an object side, a negative meniscus lens L1 having a convex surface directed toward the object side, a negative meniscus lens L2 having a convex surface directed toward the object side, a biconvex positive lens L3, a biconvex positive lens L4, and a negative meniscus lens L5 having a convex surface directed toward an image side.

An aperture stop S is disposed between the biconvex positive lens L3 and the biconvex positive lens L4.

An aspheric surface is provided to a total of eight surfaces namely, both side surfaces of the negative meniscus lens L2, both side surfaces of the biconvex positive lens L3, both side surfaces of the biconvex positive lens L4, and both side surfaces of the negative meniscus lens L5.

A wide-angle optical system according to the example 7 includes in order from an object side, a negative meniscus lens L1 having a convex surface directed toward the object side, a negative meniscus lens L2 having a convex surface directed toward the object side, a biconvex positive lens L3, a biconvex positive lens L4, and a negative meniscus lens L5 having a convex surface directed toward an image side.

An aperture stop S is disposed between the biconvex positive lens L3 and the biconvex positive lens L4.

An aspheric surface is provided to a total of six surfaces namely, both side surfaces of the negative meniscus lens L2, both side surfaces of the biconvex positive lens L3, and both side surfaces of the biconvex positive lens L4.

A wide-angle optical system according to the example 8 includes in order from an object side, a negative meniscus lens L1 having a convex surface directed toward the object side, a negative meniscus lens L2 having a convex surface directed toward the object side, a biconvex positive lens L3, a biconvex positive lens L4, and a biconcave negative lens L5.

The aperture stop S is disposed between the biconvex positive lens L3 and the biconvex positive lens L4.

An aspheric surface is provided to a total of eight surfaces namely, both side surfaces of the negative meniscus lens L2, both side surfaces of the biconvex positive lens L3, both side surfaces of the biconvex positive lens L4, and both side surfaces of the biconcave negative lens L5.

A wide-angle optical system according to the example 9 includes in order from an object side, a negative meniscus lens L1 having a convex surface directed toward the object side, a negative meniscus lens L2 having a convex surface directed toward the object side, a biconvex positive lens L3, a biconvex positive lens L4, and a negative meniscus lens L5 having a convex surface directed toward an image side.

An aperture stop S is disposed between the biconvex positive lens L3 and the biconvex positive lens L4.

An aspheric surface is provided to a total of eight surfaces namely, both side surfaces of the negative meniscus lens L2, both side surfaces of the biconvex positive lens L3, both side surfaces of the biconvex positive lens L4, and both side surfaces of the negative meniscus lens L5.

A wide-angle optical system according to the example 10 includes in order from an object side, a negative meniscus lens L1 having a convex surface directed toward the object side, a negative meniscus lens L2 having a convex surface directed toward the object side, a biconvex positive lens L3, a biconvex positive lens L4, and a negative meniscus lens L5 having a convex surface directed toward an image side.

An aperture stop S is disposed between the biconvex positive lens L3 and the biconvex positive lens L4.

An aspheric surface is provided to a total of eight surfaces namely, both side surfaces of the negative meniscus lens L2, both side surfaces of the biconvex positive lens L3, both side surfaces of the biconvex positive lens L4, and both side surfaces of the negative meniscus lens L5.

Figure 11:
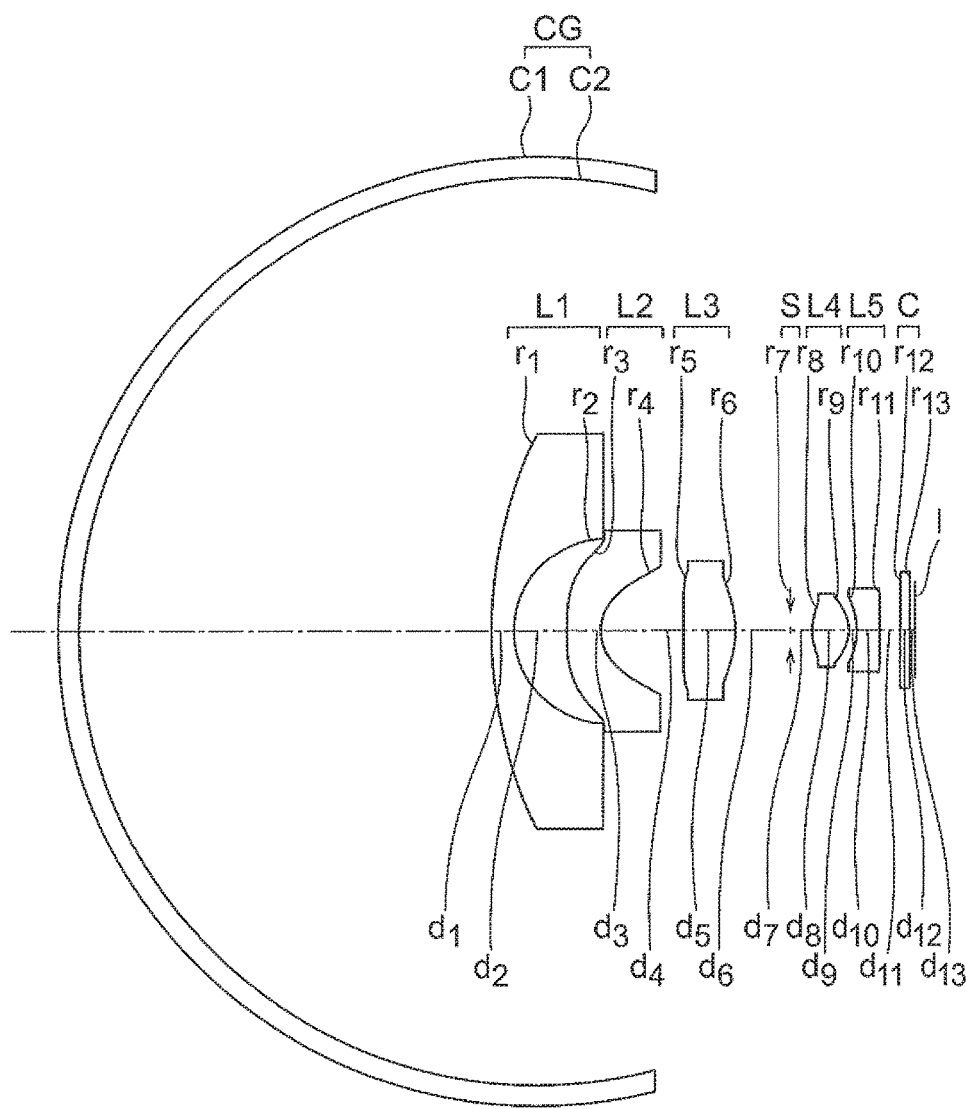
FIG. 11 is a cross-sectional view of an optical system according to an example 11 of the present invention.

A wide-angle optical system according to an example 11, as shown in FIG. 11, includes in order from an object side, an optical member CG, a negative meniscus lens L1 having a convex surface directed toward the object side, a negative meniscus lens L2 having a convex surface directed toward the object side, a biconvex positive lens L3, a biconvex positive lens L4, a negative meniscus lens L4 having a convex surface directed toward an image side. The optical system including the negative meniscus lens L1, the negative meniscus lens L2, the biconvex positive lens L3, an aperture stop S, the biconvex positive lens L4, and the negative meniscus lens L5 is same as the optical system according to the example 1.

FIG. 11 is a schematic diagram illustrating that the optical member CG can be disposed. Therefore, a size and a position of the optical member CG have not been depicted accurately with respect to sizes and positions of the lenses.

The optical member CG is a member in the form of a plate, and both an object-side surface and an image-side surface thereof are curved surfaces. In FIG. 11, both the object-side surface and the image-side surface being curved surfaces, an overall shape of the optical member CG is hemispherical. In the example 11, a thickness of the optical member CG, or in other words, a distance between the object-side surface and the image-side surface, is constant. However, the thickness of the optical member CG may not be constant.

Moreover, as it will be described later, the optical member CG is disposed at a position only 16.50 mm away on the object side from the object-side surface of the first lens. However, the optical member CG may be disposed at a position shifted frontward or rearward from the abovementioned position. Moreover, a radius of curvature and the thickness of the optical member CG mentioned here is an example, and are not limited to the radius of curvature and the thickness mentioned here.

A material that allows light to transmit through has been used for the optical member CG. Consequently, light from an object passes through the optical member CG and is incident on the negative meniscus lens L1. The optical member CG is disposed such that a curvature center of the image-side surface substantially coincides with a position of an entrance pupil. Consequently, a new aberration due to the optical member CG hardly occurs. In other words, an imaging performance of the optical system according to the example 11 is not different from an imaging performance of the optical system according to the example 1.

The optical member CG functions as a cover glass. In this case, the optical member CG corresponds to an observation window provided at an outer covering of a capsule endoscope. Therefore, the optical system according to the example 11 can be used for an optical system of a capsule endoscope. The optical systems according to the example 1 to the example 10 can also be used for an optical system of an endoscope.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens and *denotes an aspheric surface, stop denotes an aperture stop.

Further, in Various data, f denotes a focal length of the entire system, FNO. denotes an F number, ω denotes a half angle of view, IH denotes an image height, BF denotes a back focus, LTL denotes a lens total length of the optical system. Further, back focus is a unit which is expressed upon air conversion of a distance from a rearmost lens surface to a paraxial image surface. The lens total length is a distance from a frontmost lens surface to the rearmost lens surface plus back focus.

Moreover, the example 11 is an example in which, the optical member CG is disposed on the object side of the wide-angle optical system according to the example 1. In surface data of the example 11, C1 denotes the object-side surface of the optical member CG and C2 denotes the image-side surface of the optical member CG. Aspheric surface data and various data of the example 11 being same as the aspheric surface data and various data of the example 1, description thereof is omitted here.

A shape of an aspheric surface is defined by the following expression where the direction of the optical axis is represented by z, the direction orthogonal to the optical axis is represented by y, a conical coefficient is represented by K, aspheric surface coefficients are represented by A4, A6, A8, A10, A12 . . .

$$Z=(y^2/r)/[1+\{1-(1+k)(y/r)^2\}^{1/2}]+A4y^4+A6y^6+A8y^8+A10y^{10}+A12y^{12}+ \ldots$$

Further, in the aspherical surface coefficients, 'e-n' (where, n is an integral number) indicates '$10^{-n}$'. Moreover, these symbols are commonly used in the following numerical data for each example.

Example 1

| Unit mm | | | | |
|---|---|---|---|---|
| Surface data | | | | |
| Surface no. | r | d | nd | vd |
| Object plane | ∞ | ∞ | | |
| 1 | 17.935 | 0.90 | 1.88300 | 40.76 |
| 2 | 3.671 | 2.06 | | |
| 3* | 15.663 | 1.34 | 1.52550 | 55.20 |
| 4* | 1.804 | 3.21 | | |
| 5* | 373.647 | 2.04 | 1.61441 | 25.11 |
| 6* | −3.781 | 2.16 | | |
| 7 (Stop) | ∞ | 0.86 | | |
| 8* | 2.343 | 1.44 | 1.52550 | 55.20 |
| 9* | −1.359 | 0.30 | | |
| 10 | −2.873 | 0.90 | 1.95906 | 17.47 |
| 11 | −50.789 | 0.80 | | |
| 12 | ∞ | 0.40 | 1.54429 | 69.85 |

-continued

Unit mm

| 13 | ∞ | 0.20 |
| Image plane | ∞ | |

Aspherical surface data

3rd surface k = 0.000
A4 = 1.58355e-02, A6 = -1.75373e-03, A8 = 1.60983e-04,
A10 = -6.41150e-06

4th surface k = -0.553
A4 = 1.13072e-02, A6 = -3.93904e-03, A8 = 1.23756e-03,
A10 = -1.69033e-04

5th surface k = 0.000
A4 = -2.13008e-04, A6 = 9.58301e-04, A8 = -5.94675e-06

6th surface k = 0.000
A4 = 8.89321e-03, A6 = -6.16419e-04, A8 = 1.08350e-04

8th surface k = 0.000
A4 = -3.31522e-02, A6 = 8.12028e-03, A8 = -7.63407e-03

9th surface k = -0.399
A4 = 7.51855e-02, A6 = -3.67668e-03, A8 = -2.32365e-03

Various data

| f | 0.75 |
| FNO. | 2.060 |
| ω | 110 |
| IH | 1.869 |
| BF (in air) | 1.26 |
| LTL (in air) | 16.46 |

Example 2

Unit mm

Surface data

| Surface no. | r | d | nd | vd |
|---|---|---|---|---|
| Object plane | ∞ | ∞ | | |
| 1 | 19.023 | 1.00 | 1.77250 | 49.60 |
| 2 | 3.584 | 3.38 | | |
| 3* | -190.678 | 1.74 | 1.52550 | 55.20 |
| 4* | 1.877 | 1.56 | | |
| 5* | 31.953 | 2.00 | 1.61441 | 25.11 |
| 6* | -3.639 | 2.05 | | |
| 7 (Stop) | ∞ | 0.90 | | |
| 8* | 2.200 | 1.62 | 1.52550 | 55.20 |
| 9* | -1.201 | 0.20 | | |
| 10 | -3.153 | 1.06 | 1.95906 | 17.47 |
| 11 | -78.333 | 0.70 | | |
| 12 | ∞ | 0.40 | 1.54429 | 69.85 |
| 13 | ∞ | 0.20 | | |
| Image plane | ∞ | | | |

Aspherical surface data

3rd surface k = 0.000
A4 = 1.23410e-02, A6 = -2.01502e-03, A8 = 1.43358e-04,
A10 = -4.28177e-06

-continued

Unit mm

4th surface k = -0.531
A4 = -3.39617e-04, A6 = -7.19450e-03, A8 = 1.17170e-03,
A10 = -1.11213e-04

5th surface k = 0.000
A4 = 2.65384e-03, A6 = 8.93452e-04, A8 = -1.62532e-04

6th surface k = 0.000
A4 = 1.35268e-02, A6 = -1.46805e-03, A8 = 1.22028e-04

8th surface k = 0.000
A4 = -2.89678e-02, A6 = 1.54762e-02, A8 = -3.01779e-03

9th surface k = -0.731
A4 = 1.08171e-01, A6 = -1.85007e-02, A8 = 7.30958e-03

Various data

| f | 0.74 |
| FNO. | 2.085 |
| ω | 110 |
| IH | 1.890 |
| BF (in air) | 1.16 |
| LTL (in air) | 16.66 |

Example 3

Unit mm

Surface data

| Surface no. | r | d | nd | vd |
|---|---|---|---|---|
| Object plane | ∞ | ∞ | | |
| 1 | 18.077 | 0.90 | 1.88300 | 40.76 |
| 2 | 3.821 | 3.48 | | |
| 3* | 44.636 | 1.81 | 1.52550 | 55.20 |
| 4* | 1.636 | 1.57 | | |
| 5* | 10.850 | 2.00 | 1.61441 | 25.11 |
| 6* | -4.042 | 2.23 | | |
| 7 (Stop) | ∞ | 0.86 | | |
| 8* | 2.058 | 1.70 | 1.52550 | 55.20 |
| 9* | -1.131 | 0.20 | | |
| 10 | -2.455 | 0.90 | 1.95906 | 17.47 |
| 11 | -15.449 | 0.70 | | |
| 12 | ∞ | 0.40 | 1.54429 | 69.85 |
| 13 | ∞ | 0.20 | | |
| Image plane | ∞ | | | |

Aspherical surface data

3rd surface k = 0.000
A4 = 1.24086e-02, A6 = -2.01945e-03, A8 = 1.22908e-04,
A10 = -2.72775e-06

4th surface k = -0.702
A4 = 3.80078e-03, A6 = -8.18674e-03, A8 = 1.13821e-03,
A10 = -7.48142e-05

5th surface k = 0.000
A4 = 6.79552e-03, A6 = 8.14445e-04, A8 = -1.18537e-04

-continued

| Unit mm |
|---|

| 6th surface |
|---| k = 0.000
A4 = 1.37232e-02, A6 = -7.22537e-04, A8 = 7.25358e-06

| 8th surface |
|---| k = 0.000
A4 = -2.94252e-02, A6 = 1.11550e-02, A8 = -3.20349e-03

| 9th surface |
|---| k = -0.643
A4 = 1.34760e-01, A6 = -2.30198e-02, A8 = 6.63069e-03

| Various data |
|---|

| | |
|---|---|
| f | 0.72 |
| FNO. | 2.069 |
| ω | 110 |
| IH | 1.894 |
| BF (in air) | 1.16 |
| LTL (in air) | 16.81 |

Example 4

| Unit mm |
|---|

| Surface data |
|---|

| Surface no. | r | d | nd | vd |
|---|---|---|---|---|
| Object plane | ∞ | ∞ | | |
| 1 | 15.954 | 0.90 | 1.95375 | 32.32 |
| 2 | 3.918 | 3.50 | | |
| 3* | 40.928 | 1.85 | 1.52550 | 55.20 |
| 4* | 1.425 | 1.55 | | |
| 5* | 5.713 | 2.38 | 1.61441 | 25.11 |
| 6* | -4.529 | 2.36 | | |
| 7 (Stop) | ∞ | 0.20 | | |
| 8* | 3.045 | 1.77 | 1.52550 | 55.20 |
| 9* | -0.980 | 0.20 | | |
| 10 | -1.619 | 0.90 | 1.61441 | 25.11 |
| 11 | -5.056 | 0.70 | | |
| 12 | ∞ | 0.40 | 1.54429 | 69.85 |
| 13 | ∞ | 0.20 | | |
| Image plane | ∞ | | | |

| Aspherical surface data |
|---|

| 3rd surface |
|---| k = 0.000
A4 = 1.36409e-02, A6 = -2.04312e-03, A8 = 1.14184e-04,
A10 = -2.40000e-06

| 4th surface |
|---| k = -0.797
A4 = 9.92391e-03, A6 = -8.90064e-03, A8 = 1.11380e-03,
A10 = -6.56583e-05

| 5th surface |
|---| k = 0.000
A4 = 6.66084e-03, A6 = 9.36028e-04, A8 = -1.01318e-04

| 6th surface |
|---| k = 0.000
A4 = 1.23106e-02, A6 = -7.37941e-04, A8 = 2.55699e-05

| 8th surface |
|---| k = 0.000
A4 = -5.55503e-02, A6 = -7.88071e-03, A8 = -4.02901e-02

-continued

| Unit mm |
|---|

| 9th surface |
|---| k = -0.623
A4 = 9.79481e-02, A6 = -1.29617e-02, A8 = -7.49687e-03

| Various data |
|---|

| | |
|---|---|
| f | 0.66 |
| FNO. | 2.080 |
| ω | 110 |
| IH | 1.962 |
| BF (in air) | 1.16 |
| LTL (in air) | 16.77 |

Example 5

| Unit mm |
|---|

| Surface data |
|---|

| Surface no. | r | d | nd | vd |
|---|---|---|---|---|
| Object plane | ∞ | ∞ | | |
| 1 | 17.859 | 0.90 | 1.88300 | 40.76 |
| 2 | 3.827 | 3.52 | | |
| 3* | 6.735 | 1.30 | 1.52550 | 55.20 |
| 4* | 1.281 | 1.64 | | |
| 5* | 6.908 | 2.23 | 1.61441 | 25.11 |
| 6* | -4.299 | 2.06 | | |
| 7 (Stop) | ∞ | 0.56 | | |
| 8* | 2.886 | 1.78 | 1.52550 | 55.20 |
| 9* | -1.282 | 0.20 | | |
| 10 | -2.298 | 0.50 | 1.61441 | 25.11 |
| 11 | -9.748 | 0.50 | | |
| 12 | ∞ | 0.30 | 1.51633 | 64.14 |
| 13 | ∞ | 0.50 | | |
| 14 | ∞ | 0.40 | 1.54429 | 69.85 |
| 15 | ∞ | 0.11 | | |
| Image plane | ∞ | | | |

| Aspherical surface data |
|---|

| 3rd surface |
|---| k = 0.000
A4 = 6.67696e-03, A6 = -2.16371e-03, A8 = 1.31847e-04,
A10 = -2.39546e-06

| 4th surface |
|---| k = -0.836
A4 = -1.57797e-03, A6 = -8.35115e-03, A8 = 8.78249e-04,
A10 = -4.68590e-05

| 5th surface |
|---| k = 0.000
A4 = 2.37292e-03, A6 = 2.55297e-03, A8 = -2.95201e-04

| 6th surface |
|---| k = 0.000
A4 = 1.00538e-02, A6 = 6.55191e-04, A8 = -1.22153e-04

| 8th surface |
|---| k = 0.000
A4 = -2.54467e-02, A6 = 1.10562e-02, A8 = -7.68505e-04

| 9th surface |
|---| k = -0.890
A4 = 5.37822e-02, A6 = -1.59743e-02, A8 = 5.58946e-03

| Various data |
|---|

| | |
|---|---|
| f | 0.80 |
| FNO. | 2.097 |

-continued

Unit mm

| | |
|---|---|
| ω | 110 |
| IH | 1.885 |
| BF (in air) | 1.57 |
| LTL (in air) | 16.25 |

Example 6

Unit mm

Surface data

| Surface no. | r | d | nd | νd |
|---|---|---|---|---|
| Object plane | ∞ | ∞ | | |
| 1 | 18.400 | 0.90 | 1.88300 | 40.76 |
| 2 | 4.650 | 4.00 | | |
| 3* | 22.509 | 1.53 | 1.52550 | 55.20 |
| 4* | 1.311 | 1.73 | | |
| 5* | 5.104 | 2.54 | 1.61441 | 25.11 |
| 6* | −4.255 | 1.76 | | |
| 7 (Stop) | ∞ | 0.14 | | |
| 8* | 3.151 | 1.69 | 1.52550 | 55.20 |
| 9* | −0.958 | 0.10 | | |
| 10* | −1.272 | 0.50 | 1.61441 | 25.11 |
| 11* | −2.703 | 0.40 | | |
| 12 | ∞ | 0.30 | 1.51633 | 64.14 |
| 13 | ∞ | 0.50 | | |
| 14 | ∞ | 0.40 | 1.54429 | 69.85 |
| 15 | ∞ | 0.11 | | |
| Image plane | ∞ | | | |

Aspherical surface data

3rd surface k = 0.000
A4 = 1.17385e-02, A6 = −1.84005e-03, A8 = 9.22521e-05,
A10 = −1.60746e-06

4th surface k = −0.854
A4 = 1.94426e-02, A6 = −1.02794e-02, A8 = 9.26569e-04,
A10 = −3.88434e-05

5th surface k = 0.000
A4 = −1.63411e-03, A6 = 2.86964e-03, A8 = −2.76546e-04,
A10 = 1.10422e-06

6th surface k = 0.000
A4 = 1.15753e-02, A6 = 4.42631e-04, A8 = −1.07688e-04,
A10 = 1.92305e-06

8th surface k = 0.000
A4 = −1.82440e-02, A6 = −2.25230e-02, A8 = −3.65954e-03,
A10 = −3.06200e-02

9th surface k = −0.711
A4 = 1.21196e-01, A6 = −1.03530e-01, A8 = 2.30865e-02,
A10 = 7.89597e-04

10th surface k = 0.000
A4 = 4.36412e-02, A6 = −1.18056e-01, A8 = 9.29479e-03,
A10 = 5.84465e-02

-continued

Unit mm

11th surface k = 0.732
A4 = −1.28579e-02, A6 = −2.29685e-02, A8 = 1.53332e-02,
A10 = 2.95746e-03

Various data

| | |
|---|---|
| f | 0.70 |
| FNO. | 1.987 |
| ω | 110 |
| IH | 1.980 |
| BF (in air) | 1.47 |
| LTL (in air) | 16.36 |

Example 7

Unit mm

Surface data

| Surface no. | r | d | nd | νd |
|---|---|---|---|---|
| Object plane | ∞ | ∞ | | |
| 1 | 18.300 | 0.90 | 1.88300 | 40.76 |
| 2 | 3.879 | 3.66 | | |
| 3* | 72.920 | 1.89 | 1.52550 | 55.20 |
| 4* | 1.584 | 1.46 | | |
| 5* | 7.265 | 2.04 | 1.61441 | 25.11 |
| 6* | −3.948 | 2.07 | | |
| 7 (Stop) | ∞ | 0.23 | | |
| 8* | 5.284 | 1.73 | 1.52550 | 55.20 |
| 9* | −1.100 | 0.20 | | |
| 10 | −2.479 | 0.60 | 1.61441 | 25.11 |
| 11 | −5.796 | 0.50 | | |
| 12 | ∞ | 0.30 | 1.51633 | 64.14 |
| 13 | ∞ | 0.50 | | |
| 14 | ∞ | 0.40 | 1.54429 | 69.85 |
| 15 | ∞ | 0.11 | | |
| Image plane | ∞ | | | |

Aspherical surface data

3rd surface k = 0.000
A4 = 1.37784e-02, A6 = −2.04668e-03, A8 = 1.14711e-04,
A10 = −2.45770e-06

4th surface k = −0.750
A4 = 4.83073e-03, A6 = −8.98969e-03, A8 = 1.09118e-03,
A10 = −6.12778e-05

5th surface k = 0.000
A4 = 2.87497e-03, A6 = 9.04389e-04, A8 = −1.83299e-04

6th surface k = 0.000
A4 = 1.37023e-02, A6 = −1.21971e-03, A8 = 3.50341e-05

8th surface k = 0.000
A4 = −5.29258e-02, A6 = −6.74808e-03, A8 = 9.92342e-03

9th surface k = −0.732
A4 = 6.15109e-02, A6 = −1.75265e-02, A8 = 1.94271e-03

-continued

Unit mm

Various data

| | |
|---|---|
| f | 0.70 |
| FNO. | 2.091 |
| ω | 110 |
| IH | 1.908 |
| BF (in air) | 1.57 |
| LTL (in air) | 16.36 |

Example 8

Unit mm

Surface data

| Surface no. | r | d | nd | vd |
|---|---|---|---|---|
| Object plane | ∞ | ∞ | | |
| 1 | 18.416 | 0.90 | 1.88300 | 40.76 |
| 2 | 3.953 | 3.43 | | |
| 3* | 43.521 | 1.76 | 1.52559 | 56.45 |
| 4* | 1.544 | 1.60 | | |
| 5* | 6.852 | 2.30 | 1.61421 | 25.60 |
| 6* | −4.134 | 2.18 | | |
| 7 (Stop) | ∞ | 0.32 | | |
| 8* | 3.090 | 1.80 | 1.52559 | 56.45 |
| 9* | −1.190 | 0.20 | | |
| 10* | −4.302 | 0.70 | 1.61421 | 25.60 |
| 11* | 12.162 | 0.30 | | |
| 12 | ∞ | 0.30 | 1.51633 | 64.14 |
| 13 | ∞ | 0.30 | | |
| 14 | ∞ | 0.40 | 1.51633 | 64.14 |
| 15 | ∞ | 0.11 | | |
| Image plane | ∞ | | | |

Aspherical surface data

3rd surface k = 0.000
A4 = 1.28114e−02, A6 = −2.02022e−03, A8 = 1.16923e−04,
A10 = −2.48116e−06

4th surface k = −0.754
A4 = 5.39837e−03, A6 = −8.85606e−03, A8 = 1.10633e−03,
A10 = −6.18777e−05

5th surface k = 0.000
A4 = 2.98401e−03, A6 = 9.43212e−04, A8 = −1.72887e−04,
A10 = 3.47897e−06

6th surface k = 0.000
A4 = 1.26769e−02, A6 = −1.06519e−03, A8 = 3.01848e−05,
A10 = −4.69167e−07

8th surface k = 0.000
A4 = −2.98223e−02, A6 = −4.85028e−03, A8 = 1.79517e−02,
A10 = −2.32426e−03

9th surface k = −0.772
A4 = 9.59927e−02, A6 = −2.25784e−02, A8 = −1.94755e−02,
A10 = 1.29640e−02

10th surface k = 0.000
A4 = 2.43671e−02, A6 = −3.31337e−02, A8 = −1.38058e−02,
A10 = 8.27829e−03

-continued

Unit mm

11th surface k = 0.000
A4 = 2.57114e−02, A6 = −3.06656e−02, A8 = 4.72342e−03,
A10 = 2.58777e−04

Various data

| | |
|---|---|
| f | 0.70 |
| FNO. | 2.045 |
| ω | 110 |
| IH | 1.802 |
| BF (in air) | 1.17 |
| LTL (in air) | 16.36 |

Example 9

Unit mm

Surface data

| Surface no. | r | d | nd | vd |
|---|---|---|---|---|
| Object plane | ∞ | ∞ | | |
| 1 | 18.416 | 0.90 | 1.88300 | 40.76 |
| 2 | 3.961 | 3.40 | | |
| 3* | 42.888 | 1.71 | 1.52559 | 56.45 |
| 4* | 1.534 | 1.65 | | |
| 5* | 7.258 | 2.30 | 1.61421 | 25.60 |
| 6* | −4.038 | 2.22 | | |
| 7(Stop) | ∞ | 0.32 | | |
| 8* | 2.919 | 1.80 | 1.52559 | 56.45 |
| 9* | −1.167 | 0.20 | | |
| 10* | −2.863 | 0.70 | 1.61421 | 25.60 |
| 11* | −50.000 | 0.30 | | |
| 12 | ∞ | 0.30 | 1.51633 | 64.14 |
| 13 | ∞ | 0.30 | | |
| 14 | ∞ | 0.40 | 1.51633 | 64.14 |
| 15 | ∞ | 0.11 | | |
| Image plane | ∞ | | | |

Aspherical surface data

3rd surface k = 0.000
A4 = 1.30092e−02, A6 = −2.02235e−03, A8 = 1.14642e−04,
A10 = −2.40550e−06

4th surface k = −0.762
A4 = 4.83299e−03, A6 = −8.90540e−03, A8 = 1.10715e−03,
A10 = −5.98191e−05

5th surface k = 0.000
A4 = 1.54350e−03, A6 = 9.26327e−04, A8 = −1.81763e−04,
A10 = 6.66033e−06

6th surface k = 0.000
A4 = 1.15410e−02, A6 = −1.02216e−03, A8 = 4.72210e−05,
A10 = −8.82448e−07

8th surface k = 0.000
A4 = −2.78987e−02, A6 = 1.66257e−03, A8 = 6.44183e−03,
A10 = 3.43928e−03

9th surface k = −0.835
A4 = 1.04148e−01, A6 = −2.37305e−02, A8 = −2.81227e−02,
A10 = 1.72198e−02

-continued

| Unit mm |
|---|
| 10th surface | k = 0.000
A4 = 5.29809e−02, A6 = −4.94964e−02, A8 = −2.17119e−02,
A10 = 1.47986e−02

| 11th surface |
|---| k = 0.000
A4 = 4.85141e−02, A6 = −5.19321e−02, A8 = 1.25070e−02,
A10 = −1.02400e−03

| Various data | |
|---|---|
| f | 0.70 |
| FNO. | 2.025 |
| ω | 110 |
| IH | 1.814 |
| BF(in air) | 1.17 |
| LTL(in air) | 16.36 |

Example 10

| Unit mm | | | | |
|---|---|---|---|---|
| Surface data | | | | |
| Surface no. | r | d | nd | vd |
| Object plane | ∞ | ∞ | | |
| 1 | 19.000 | 0.90 | 1.88300 | 40.76 |
| 2 | 5.663 | 4.31 | | |
| 3* | 28.394 | 1.53 | 1.52550 | 55.20 |
| 4* | 1.309 | 1.97 | | |
| 5* | 6.083 | 2.16 | 1.61441 | 25.11 |
| 6* | −4.289 | 1.69 | | |
| 7(Stop) | ∞ | 0.11 | | |
| 8* | 3.488 | 1.62 | 1.52550 | 55.20 |
| 9* | −0.813 | 0.10 | | |
| 10* | −1.119 | 0.50 | 1.61441 | 25.11 |
| 11* | −2.770 | 0.40 | | |
| 12 | ∞ | 0.30 | 1.51633 | 64.14 |
| 13 | ∞ | 0.50 | | |
| 14 | ∞ | 0.40 | 1.54429 | 69.85 |
| 15 | ∞ | 0.11 | | |
| Image plane | ∞ | | | |

| Aspherical surface data |
|---|
| 3rd surface | k = 0.000
A4 = 1.19909e−02, A6 = −1.83652e−03, A8 = 9.20249e−05,
A10 = −1.61630e−06

| 4th surface |
|---| k = −0.854
A4 = 1.75517e−02, A6 = −1.03019e−02, A8 = 9.26201e−04,
A10 = −3.90454e−05

| 5th surface |
|---| k = 0.000
A4 = −4.63397e−04, A6 = 2.90018e−03, A8 = −2.92313e−04,
A10 = −3.23995e−07

| 6th surface |
|---| k = 0.000
A4 = 1.31252e−02, A6 = 4.55045e−04, A8 = −1.11808e−04,
A10 = 1.63501e−06

| 8th surface |
|---| k = 0.000
A4 = −3.87854e−02, A6 = −2.21237e−02, A8 = −1.12268e−04,
A10 = −1.62412e−01

-continued

| Unit mm |
|---|
| 9th surface | k = −0.719
A4 = 1.42583e−01, A6 = −1.15221e−01, A8 = 4.87687e−02,
A10 = −3.81795e−02

| 10th surface |
|---| k = 0.000
A4 = 2.21906e−02, A6 = −1.06222e−01, A8 = 7.86827e−03,
A10 = 4.72639e−02

| 11th surface |
|---| k = 2.570
A4 = −1.61930e−02, A6 = −2.83230e−02, A8 = 2.19284e−02,
A10 = 8.25400e−04

| Various data | |
|---|---|
| f | 0.70 |
| FNO. | 2.744 |
| ω | 100 |
| IH | 1.904 |
| BF(in air) | 1.47 |
| LTL(in air) | 16.36 |

Example 11

| Unit mm | | | | |
|---|---|---|---|---|
| Surface data | | | | |
| Surface no. | r | d | nd | vd |
| Object plane | ∞ | ∞ | | |
| C1 | 18.000 | 1.00 | 1.5896 | 30.00 |
| C2 | 17.000 | 16.5 | | |
| 1 | 17.935 | 0.90 | 1.88300 | 40.76 |
| 2 | 3.671 | 2.06 | | |
| 3* | 15.663 | 1.34 | 1.52550 | 55.20 |
| 4* | 1.804 | 3.21 | | |
| 5* | 373.647 | 2.04 | 1.61441 | 25.11 |
| 6* | −3.781 | 2.16 | | |
| 7(Stop) | ∞ | 0.86 | | |
| 8* | 2.343 | 1.44 | 1.52550 | 55.20 |
| 9* | −1.359 | 0.30 | | |
| 10 | −2.873 | 0.90 | 1.95906 | 17.47 |
| 11 | −50.789 | 0.80 | | |
| 12 | ∞ | 0.40 | 1.54429 | 69.85 |
| 13 | ∞ | 0.20 | | |
| Image plane | ∞ | | | |

An amount of distortion calculated by using the stereographic projection method is shown below.

Example 1

TABLE 1

| ω [°] | y [mm] | Y [mm] | DT [%] |
|---|---|---|---|
| 0 | 0 | 0.000 | 0 |
| 10 | 0.132 | 0.132 | 0.398 |
| 20 | 0.270 | 0.266 | 1.752 |
| 30 | 0.422 | 0.404 | 4.397 |
| 40 | 0.595 | 0.549 | 8.437 |
| 50 | 0.794 | 0.703 | 12.985 |
| 60 | 1.016 | 0.870 | 16.744 |
| 70 | 1.252 | 1.056 | 18.609 |
| 80 | 1.476 | 1.265 | 16.705 |
| 90 | 1.664 | 1.508 | 10.379 |

TABLE 1-continued

| ω [°] | y [mm] | Y [mm] | DT [%] |
|---|---|---|---|
| 100 | 1.799 | 1.797 | 0.148 |
| 110 | 1.869 | 2.153 | −13.171 |

Example 2

TABLE 2

| ω [°] | y [mm] | Y [mm] | DT [%] |
|---|---|---|---|
| 0 | 0.000 | 0.000 | 0 |
| 10 | 0.131 | 0.130 | 0.380 |
| 20 | 0.267 | 0.262 | 1.611 |
| 30 | 0.414 | 0.399 | 3.853 |
| 40 | 0.580 | 0.542 | 7.147 |
| 50 | 0.770 | 0.694 | 10.902 |
| 60 | 0.977 | 0.859 | 13.772 |
| 70 | 1.195 | 1.042 | 14.712 |
| 80 | 1.417 | 1.249 | 13.453 |
| 90 | 1.629 | 1.488 | 9.474 |
| 100 | 1.799 | 1.773 | 1.433 |
| 110 | 1.890 | 2.125 | −11.083 |

Example 3

TABLE 3

| ω [°] | y [mm] | Y [mm] | DT [%] |
|---|---|---|---|
| 0 | 0.000 | 0.000 | 0 |
| 10 | 0.127 | 0.126 | 0.471 |
| 20 | 0.259 | 0.254 | 1.977 |
| 30 | 0.405 | 0.386 | 4.752 |
| 40 | 0.571 | 0.525 | 8.921 |
| 50 | 0.765 | 0.672 | 13.812 |
| 60 | 0.979 | 0.832 | 17.682 |
| 70 | 1.202 | 1.009 | 19.118 |
| 80 | 1.424 | 1.209 | 17.730 |
| 90 | 1.632 | 1.441 | 13.199 |
| 100 | 1.799 | 1.718 | 4.749 |
| 110 | 1.894 | 2.059 | −7.987 |

Example 4

TABLE 4

| ω [°] | y [mm] | Y [mm] | DT [%] |
|---|---|---|---|
| 0 | 0.000 | 0.000 | 0 |
| 10 | 0.116 | 0.116 | 0.459 |
| 20 | 0.238 | 0.233 | 1.987 |
| 30 | 0.372 | 0.354 | 4.956 |
| 40 | 0.528 | 0.481 | 9.759 |
| 50 | 0.714 | 0.616 | 15.839 |
| 60 | 0.923 | 0.763 | 20.975 |
| 70 | 1.143 | 0.926 | 23.527 |
| 80 | 1.370 | 1.109 | 23.478 |
| 90 | 1.596 | 1.322 | 20.723 |
| 100 | 1.800 | 1.575 | 14.221 |
| 110 | 1.962 | 1.888 | 3.916 |

Example 5

TABLE 5

| ω [°] | y [mm] | Y [mm] | DT [%] |
|---|---|---|---|
| 0 | 0.000 | 0.000 | 0 |
| 10 | 0.141 | 0.140 | 0.438 |
| 20 | 0.287 | 0.282 | 1.792 |
| 30 | 0.447 | 0.429 | 4.090 |
| 40 | 0.624 | 0.583 | 7.088 |
| 50 | 0.821 | 0.747 | 9.943 |
| 60 | 1.031 | 0.925 | 11.472 |
| 70 | 1.244 | 1.121 | 10.907 |
| 80 | 1.451 | 1.344 | 7.967 |
| 90 | 1.641 | 1.602 | 2.462 |
| 100 | 1.796 | 1.909 | −5.905 |
| 110 | 1.885 | 2.287 | −17.568 |

Example 6

TABLE 6

| ω [°] | y [mm] | Y [mm] | DT [%] |
|---|---|---|---|
| 0 | 0.000 | 0.000 | 0 |
| 10 | 0.123 | 0.122 | 0.270 |
| 20 | 0.250 | 0.247 | 1.229 |
| 30 | 0.387 | 0.375 | 3.232 |
| 40 | 0.543 | 0.509 | 6.667 |
| 50 | 0.726 | 0.653 | 11.187 |
| 60 | 0.929 | 0.808 | 14.982 |
| 70 | 1.141 | 0.980 | 16.458 |
| 80 | 1.357 | 1.174 | 15.507 |
| 90 | 1.574 | 1.400 | 12.490 |
| 100 | 1.792 | 1.668 | 7.416 |
| 110 | 1.980 | 1.999 | −0.966 |

Example 7

TABLE 7

| ω [°] | y [mm] | Y [mm] | DT [%] |
|---|---|---|---|
| 0 | 0.000 | 0.000 | 0 |
| 10 | 0.123 | 0.123 | 0.421 |
| 20 | 0.252 | 0.247 | 1.787 |
| 30 | 0.392 | 0.376 | 4.395 |
| 40 | 0.553 | 0.510 | 8.502 |
| 50 | 0.742 | 0.653 | 13.542 |
| 60 | 0.951 | 0.809 | 17.587 |
| 70 | 1.169 | 0.981 | 19.162 |
| 80 | 1.390 | 1.176 | 18.207 |
| 90 | 1.606 | 1.401 | 14.633 |
| 100 | 1.791 | 1.670 | 7.254 |
| 110 | 1.908 | 2.001 | −4.672 |

Example 8

TABLE 8

| ω [°] | y [mm] | Y [mm] | DT [%] |
|---|---|---|---|
| 0 | 0.000 | 0.000 | 0 |
| 10 | 0.123 | 0.123 | 0.344 |
| 20 | 0.252 | 0.247 | 1.865 |
| 30 | 0.393 | 0.376 | 4.772 |
| 40 | 0.558 | 0.510 | 9.326 |
| 50 | 0.750 | 0.653 | 14.798 |

TABLE 8-continued

| ω [°] | y [mm] | Y [mm] | DT [%] |
|---|---|---|---|
| 60 | 0.963 | 0.809 | 19.042 |
| 70 | 1.182 | 0.981 | 20.476 |
| 80 | 1.396 | 1.176 | 18.697 |
| 90 | 1.586 | 1.401 | 13.172 |
| 100 | 1.727 | 1.670 | 3.403 |
| 110 | 1.802 | 2.001 | −9.959 |

Example 9

TABLE 9

| ω [°] | y [mm] | Y [mm] | DT [%] |
|---|---|---|---|
| 0 | 0.000 | 0.000 | 0 |
| 10 | 0.123 | 0.123 | 0.357 |
| 20 | 0.252 | 0.247 | 1.922 |
| 30 | 0.394 | 0.376 | 4.931 |
| 40 | 0.560 | 0.510 | 9.693 |
| 50 | 0.755 | 0.653 | 15.482 |
| 60 | 0.970 | 0.809 | 19.930 |
| 70 | 1.190 | 0.981 | 21.221 |
| 80 | 1.400 | 1.176 | 19.030 |
| 90 | 1.587 | 1.401 | 13.217 |
| 100 | 1.731 | 1.670 | 3.646 |
| 110 | 1.814 | 2.001 | −9.356 |

Example 10

TABLE 10

| ω [°] | y [mm] | Y [mm] | DT [%] |
|---|---|---|---|
| 0 | 0.000 | 0.000 | 0 |
| 10 | 0.123 | 0.123 | 0.485 |
| 20 | 0.252 | 0.247 | 2.158 |
| 30 | 0.396 | 0.375 | 5.613 |
| 40 | 0.568 | 0.510 | 11.530 |
| 50 | 0.777 | 0.653 | 18.950 |
| 60 | 1.005 | 0.808 | 24.337 |
| 70 | 1.234 | 0.980 | 25.892 |
| 80 | 1.459 | 1.175 | 24.213 |
| 90 | 1.681 | 1.400 | 20.083 |
| 100 | 1.904 | 1.669 | 14.086 |

Next, values of conditional expressions in each example are given below.

| | Example1 | Example2 | Example3 | Example4 |
|---|---|---|---|---|
| (1)(R1L + R1R)/(R1L − R1R) | 1.51 | 1.46 | 1.54 | 1.65 |
| (2)D34/FL | 4.01 | 3.96 | 4.29 | 3.88 |
| (3)(R3L + R3R)/(R3L − R3R) | 0.98 | 0.80 | 0.46 | 0.12 |
| (4)(R5L + R5R)/(R5L − R5R) | −1.12 | −1.08 | −1.38 | −1.94 |
| (6)FL1/FL2 | 1.34 | 1.67 | 1.72 | 1.97 |
| (7)(R2R + R3L)/(R2R − R3L) | −1.01 | −1.12 | −1.36 | −1.66 |
| (8)FL3/FL | 8.03 | 7.24 | 6.95 | 6.77 |
| (9)nd1 | 1.883 | 1.773 | 1.883 | 1.954 |
| (10)vd1 | 40.76 | 49.6 | 40.76 | 32.3188 |
| (11)nd4 | 1.526 | 1.526 | 1.526 | 1.526 |
| (12)vd4 | 55.20 | 55.20 | 55.20 | 55.20 |
| (13)FL5/FL | −4.20 | −4.58 | −4.31 | −6.46 |
| (14)Φ1/FL | 19.49 | 20.67 | 21.37 | 25.00 |
| (15)2ω | 220 | 220 | 220 | 220 |
| (16)Fno | 2.06 | 2.08 | 2.07 | 2.08 |

| | Example5 | Example6 | Example7 | Example8 |
|---|---|---|---|---|
| (1)(R1L + R1R)/(R1L − R1R) | 1.55 | 1.68 | 1.54 | 1.55 |
| (2)D34/FL | 3.27 | 2.72 | 3.29 | 3.58 |
| (3)(R3L + R3R)/(R3L − R3R) | 0.23 | 0.09 | 0.30 | 0.25 |
| (4)(R5L + R5R)/(R5L − R5R) | −1.62 | −2.78 | −2.50 | −0.48 |
| (6)FL1/FL2 | 1.73 | 2.67 | 1.84 | 1.90 |
| (7)(R2R + R3L)/(R2R − R3L) | −1.46 | −1.69 | −1.56 | −1.58 |
| (8)FL3/FL | 5.78 | 5.97 | 6.33 | 6.46 |
| (9)nd1 | 1.883 | 1.883 | 1.883 | 1.883 |
| (10)vd1 | 40.76 | 40.76 | 40.76 | 40.76 |
| (11)nd4 | 1.526 | 1.526 | 1.526 | 1.526 |
| (12)vd4 | 55.20 | 55.20 | 55.20 | 56.45 |
| (13)FL5/FL | −6.22 | −6.39 | −10.72 | −7.21 |
| (14)Φ1/FL | 19.18 | 24.97 | 22.07 | 22.00 |
| (15)2ω | 220 | 220 | 220 | 220 |
| (16)Fno | 2.10 | 1.99 | 2.09 | 2.04 |

| | Example9 | Example10 |
|---|---|---|
| (1)(R1L + R1R)/(R1L − R1R) | 1.55 | 1.85 |
| (2)D34/FL | 3.62 | 2.57 |
| (3)(R3L + R3R)/(R3L − R3R) | 0.29 | 0.17 |
| (4)(R5L + R5R)/(R5L − R5R) | −1.12 | −2.35 |
| (6)FL1/FL2 | 1.91 | 3.54 |
| (7)(R2R + R3L)/(R2R − R3L) | −1.54 | −1.55 |
| (8)FL3/FL | 6.49 | 6.30 |
| (9)nd1 | 1.883 | 1.883 |
| (10)vd1 | 40.76 | 40.76 |
| (11)nd4 | 1.526 | 1.526 |
| (12)vd4 | 56.45 | 55.20 |
| (13)FL5/FL | −7.04 | −4.89 |
| (14)Φ1/FL | 21.89 | 25.13 |
| (15)2ω | 220 | 200 |
| (16)Fno | 2.02 | 2.74 |

Figure 12:
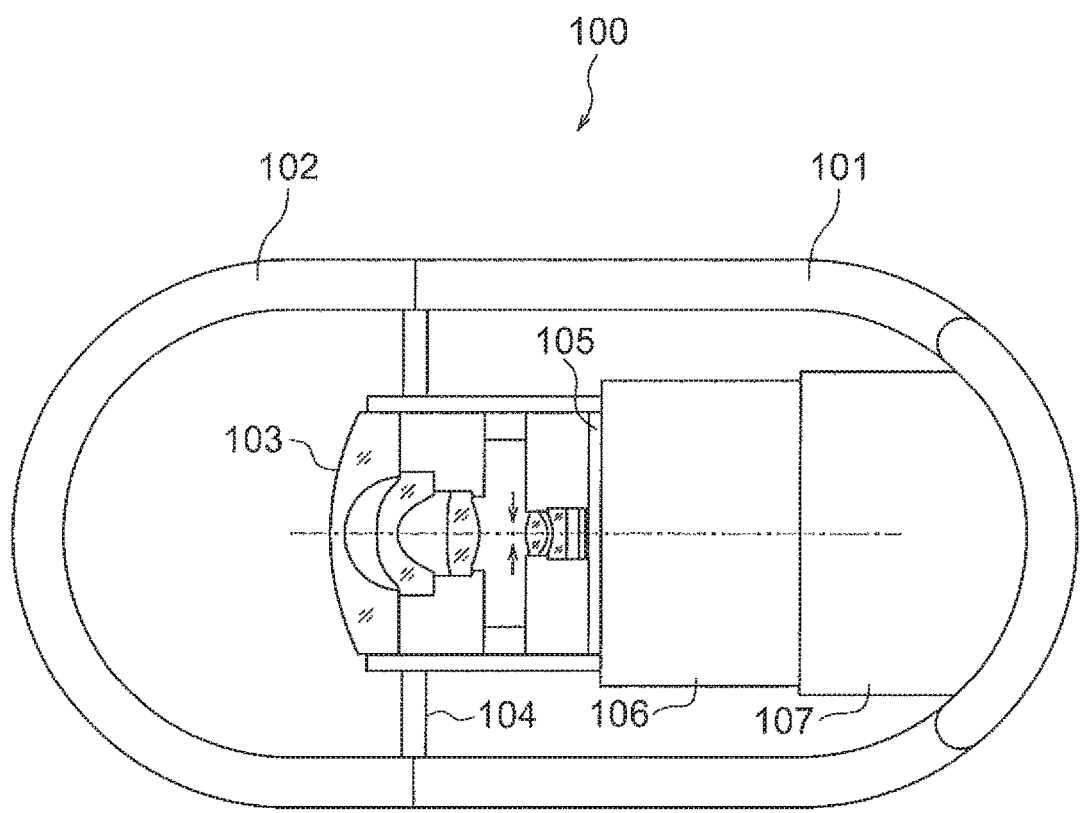
FIG. 12 is a diagram illustrating a schematic arrangement of a capsule endoscope.

FIG. 12 illustrates an example of an image pickup apparatus. In this example, the image pickup apparatus is a capsule endoscope. A capsule endoscope 100 includes a capsule cover 101 and a transparent cover 102. An outer covering f the capsule endoscope 100 is formed by the capsule cover 101 and the transparent cover 102.

The capsule cover 101 includes a central portion having a substantially circular cylindrical shape, and a bottom portion having a substantially bowl shape. The transparent cover 102 is disposed at a position facing the bottom portion, across the central portion. The transparent cover 102 is formed by a transparent member having a substantially bowl shape. The capsule cover 101 and the transparent cover 102 are connected consecutively to be mutually watertight.

An interior of the capsule endoscope 100 includes an image forming optical system 103, a illumination unit 104, an image pickup element 105, a drive control unit 106, and a signal processing unit 107. Although it is not shown in the diagram, the interior of the capsule endoscope 100 is provided with an electric-power receiving unit and a transmitting unit.

Illumination light is irradiated from the illumination unit 104. The illumination light passes through the transparent cover 102 and is irradiated to an object. Light from the object is incident on the image forming optical system 103. An optical image of the object is formed at an image position by the image forming optical system 103.

The optical image is picked up by the image pickup element 105. A drive and control of the image pickup element 105 is carried out by the drive control unit 106. Moreover, an output signal from the image pickup element 105 is processed by the signal processing unit 107 according to the requirement.

Here, for the image forming optical system 103, the wide-angle optical system according to the abovementioned example 1 for instance, is used. In such manner, the image forming optical system 103, while being small-sized, has a wide angle of view and a small F-number. Consequently, in the image forming optical system 103, a wide-angle optical image having a high resolution is achieved.

Moreover, the capsule endoscope 100, while being small-sized, includes an optical system having a wide angle of view and a small F-number. Consequently, in the capsule endoscope 100, while being small-sized, it is possible to acquire a wide-angle image with high resolution.

Figure 13A:
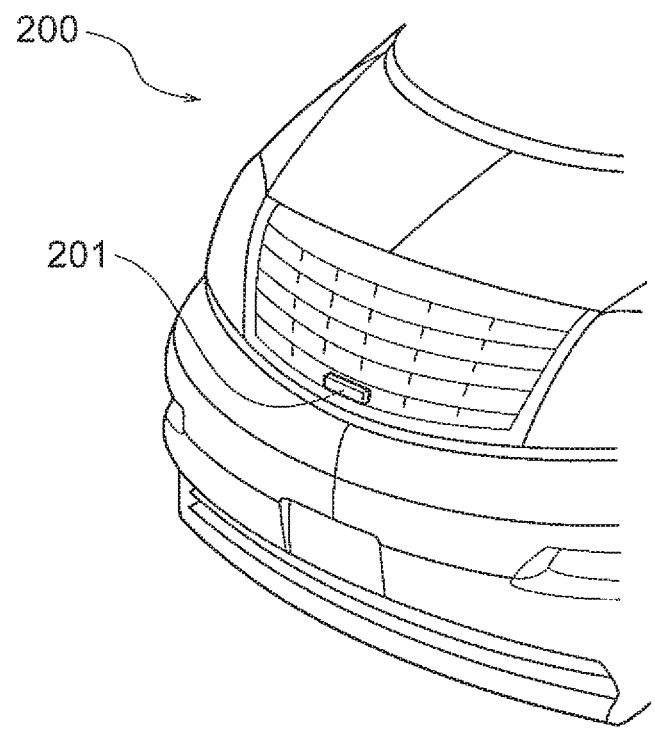
FIG. 13A is a diagram illustrating an example a car-mounted camera mounted at an outside of a car.
Figure 13B:
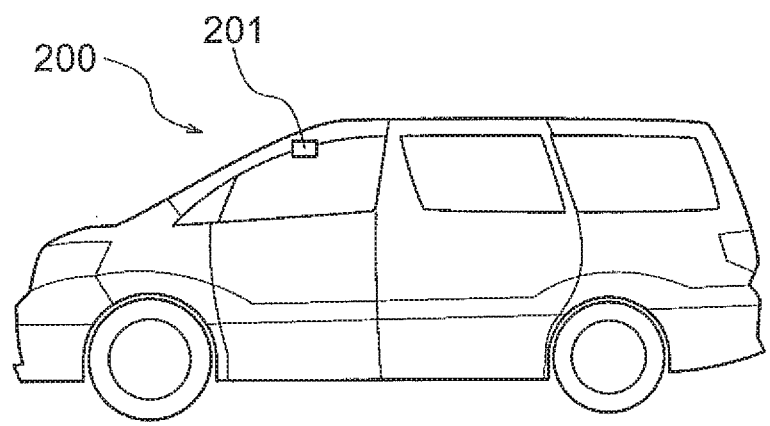
FIG. 13B is a diagram illustrating an example of a car-mounted camera mounted inside a car.

FIG. 13A and FIG. 13B are diagrams illustrating another example of an image pickup apparatus. In this example, the image pickup apparatus is a car-mounted camera. FIG. 13A is a diagram illustrating an example of a car-mounted camera mounted at an outside of a car, and FIG. 13B is a diagram illustrating an example of a car-mounted camera mounted inside a car.

As shown in FIG. 13A, a car-mounted camera 201 is provided to a front grill of an automobile 200. The car-mounted camera 201 includes an image forming optical system and an image pickup element.

For the image forming optical system of the car-mounted camera 201, the optical system according to the abovementioned example 1 is used. Consequently, an optical image of an extremely wide range (the angle of view of about 220°) is formed.

As shown in FIG. 13B, the car-mounted camera 201 is provided near a ceiling of the automobile 200. An action and an effect of the car-mounted camera 201 are as have already been described. In the car-mounted camera 201, while being small-sized, it is possible to acquire a wide-angle image with high resolution.

According to the present embodiment, it is possible to provide a wide-angle optical system which has a wide angle view, and in which, various aberrations are corrected favorably, and an image pickup apparatus equipped with such wide-angle optical system. Moreover, it is possible to provide a wide-angle optical system which has a small F-number, and in which, various aberrations are corrected favorably, and an image pickup apparatus equipped with such wide-angle optical system.

As described heretofore, the wide-angle optical system according to the present invention is suitable for a wide-angle optical system which has a wide angle of view, and in which, various aberrations are corrected favorably, and an image pickup apparatus equipped with such wide-angle optical system. Moreover, as the wide-angle optical system according to the present invention is suitable for a wide-angle optical system which has a small F-number, and in which, various aberrations are corrected favorably, and an image pickup apparatus equipped with such wide-angle optical system.

What is claimed is:

1. A wide-angle optical system comprising in order from an object side to an image side:
   a first lens element having a negative refractive power;
   a second lens element having a negative refractive power;
   a third lens element having a positive refractive power;
   an aperture stop;
   a fourth lens element having a positive refractive power; and
   a fifth lens element, wherein:
   the total number of lens elements in the wide-angle optical system is five,
   an object-side surface of the first lens element is convex toward the object side, and
   the following conditional expression (1), (2), and (3) are satisfied:

$$1.0 < (R1L + R1R)/(R1L - R1R) \leq 2.0 \quad (1),$$

$$1.7 \leq D34/FL \leq 7.0 \quad (2), \text{ and}$$

$$-0.4 \leq (R3L + R3R)/(R3L - R3R) \leq 2.0 \quad (3),$$

where,
   R1L denotes a paraxial radius of curvature of the object-side surface of the first lens element,
   R1R denotes a paraxial radius of curvature of an image-side surface of the first lens element,
   D34 denotes a distance on an optical axis from an image-side surface of the third lens element up to an object-side surface of the fourth lens element,
   FL denotes a focal length of the overall wide-angle optical system,
   R3L denotes a paraxial radius of curvature of an object-side surface of the third lens element, and
   R3R denotes a paraxial radius of curvature of the image-side surface of the third lens element.

2. A wide-angle optical system comprising in order from an object side to an image side:
   a first lens element having a negative refractive power;
   a second lens element having a negative refractive power;
   a third lens element having a positive refractive power;
   an aperture stop;
   a fourth lens element having a positive refractive power; and
   a fifth lens element having a negative refractive power, wherein:
   the total number of lenses lens elements in the wide-angle optical system is five,
   an object-side surface of the first lens element is convex toward the object side, and
   the following conditional expression (2), (3) and (4) are satisfied:

$$1.7 \leq D34/FL \leq 7.0 \quad (2),$$

$$-0.4 \leq (R3L + R3R)/(R3L - R3R) \leq 2.0 \quad (3), \text{ and}$$

$$-5.0 \leq (R5L + R5R)/(R5L - R5R) \leq -0.37 \quad (4),$$

where,
   D34 denotes a distance on an optical axis from an image-side surface of the third lens element up to an object-side surface of the fourth lens element,
   FL denotes a focal length of the overall wide-angle optical system,
   R3L denotes a paraxial radius of curvature of an object-side surface of the third lens element,
   R3R denotes a paraxial radius of curvature of the image-side surface of the third lens element,
   R5L denotes a paraxial radius of curvature of an object-side surface of the fifth lens element, and
   R5R denotes a paraxial radius of curvature of an image-side surface of the fifth lens element.

3. The wide-angle optical system according to claim 1, wherein the following conditional expressions (5) and (6) are satisfied:

$$nd2 < nd1 \quad (5), \text{ and}$$

$$0.2 \leq FL1/FL2 \leq 3.8 \quad (6),$$

where,
   nd1 denotes a refractive index for a d-line of the first lens element, nd2 denotes a refractive index for a d-line of the second lens element, FL1 denotes a focal length of the first lens element, and FL2 denotes a focal length of the second lens element.

4. The wide-angle optical system according to claim 1, wherein the following conditional expression (7) is satisfied $$-2.1 \leq (R2R+R3L)/(R2R-R3L) \leq -0.2 \quad (7)$$

where,

R2R denotes a paraxial radius of curvature of an image-side surface of the second lens element, and R3L denotes the paraxial radius of curvature of the object-side surface of the third lens element.

5. The wide-angle optical system according to claim 1, wherein the following conditional expression (8) is satisfied:

$$4.2 \leq FL3/FL \leq 12.0 \quad (8),$$

where,

FL3 denotes a focal length of the third lens element, and

FL denotes the focal length of the overall wide-angle optical system.

6. The wide-angle optical system according to claim 1, wherein the following conditional expressions (9) and (10) are satisfied:

$$1.7 \leq nd1 \leq 2.1 \quad (9), \text{ and}$$

$$25 \leq vd1 \leq 55 \quad (10),$$

where, nd1 denotes a refractive index for a d-line of the first lens element, and vd1 denotes Abbe's number for the first lens element.

7. The wide-angle optical system according to claim 1, wherein the following conditional expressions (11) and (12) are satisfied:

$$1.45 \leq nd4 \leq 1.65 \quad (11), \text{ and}$$

$$25 \leq vd4 \leq 60 \quad (12),$$

where, nd4 denotes a refractive index for a d-line of the fourth lens element, and vd4 denotes Abbe's number for the fourth lens element.

8. The wide-angle optical system according to claim 1, wherein the fifth lens element has a negative refractive power.

9. The wide angle optical system according to claim 2, wherein the following conditional expression (13) is satisfied:

$$-30 \leq FL5/FL \leq -6 \quad (13),$$

where,

FL5 denotes a focal length of the fifth lens element, and

FL denotes the focal length of the overall wide-angle optical system.

10. The wide-angle optical system according to claim 1, wherein the following conditional expression (14) is satisfied:

$$15 \leq \Phi 1/FL \leq 30 \quad (14),$$

where,

Φ1 denotes a maximum effective aperture in the first lens element, and

FL denotes the focal length of the overall wide-angle optical system.

11. The wide-angle optical system according to claim 1, wherein the following conditional expressions (15) and (16) are satisfied:

$$200° \leq 2\omega \leq 240° \quad (15), \text{ and}$$

$$2.5 \leq Fno \leq 1.5 \quad (16),$$

where,

ω denotes a maximum half angle of view, and

Fno denotes an F-number.

12. The wide-angle optical system according to claim 1, wherein each of the lens elements includes a medium of a single refractive index.

13. An image pickup apparatus comprising:

the wide-angle optical system according to claim 1; and an image pickup element.

* * * * *

UNITED STATES PATENT AND TRADEMARK OFFICE
CERTIFICATE OF CORRECTION

PATENT NO.        : 10,107,993 B2
APPLICATION NO.   : 15/208123
DATED             : October 23, 2018
INVENTOR(S)       : Takahiro Amanai It is certified that error appears in the above-identified patent and that said Letters Patent is hereby corrected as shown below:

In the Specification

Column 1, Line 11, before "which" insert --of--.

Column 1, Line 54, after "according" insert --to--.

Column 2, Line 62, delete "30," and insert --3C,--.

Column 3, Line 3, delete "55" and insert --5E--.

Column 3, Line 7, delete "60," and insert --6C,--.

Column 3, Line 7, delete "65" and insert --6E--.

Column 3, Line 15, delete "80," and insert --8C,--.

Column 3, Line 19, delete "95" and insert --9E--.

Column 3, Line 23, delete "100," and insert --10C,--.

Column 3, Line 30, after "example" insert --of--.

Column 3, Line 53, after "Therefore," insert --the--.

Column 4, Line 14, after "system" insert --of--.

Column 6, Line 13, after "(2)" insert --.--.

Column 6, Line 20, delete "expression. (2)" and insert --expression (2).--.

Signed and Sealed this
Twenty-sixth Day of February, 2019

Andrei Iancu
*Director of the United States Patent and Trademark Office*

CERTIFICATE OF CORRECTION (continued)
U.S. Pat. No. 10,107,993 B2

Column 7, Line 12, after "(3)" insert --.--.

Column 7, Line 62, delete "(4)," and insert --(4).--.

Column 8, Line 57, after "(6)" insert --.--.

Column 10, Line 58, delete "Petzval" and insert --Petzval's--.

Column 11, Line 37, after "(13)" insert --.--.

Column 11, Line 52, after "in the" insert --first--.

Column 12, Line 55, delete "35," and insert --3B,--.

Column 13, Line 4, after "(A)" insert --.--.

Column 13, Line 54, after "L4" insert --.--.

Column 24, Line 8, delete "2.58777e-04" and insert -- -2.58777e-04--.

Column 30, Line 37, delete "f" and insert --of--.

Column 31, Line 34, after "wide angle" insert --of--.

In the Claims

Column 32, Line 33, Claim 2, before "lens" delete "lenses".